(12) United States Patent
Shimizu et al.

(10) Patent No.: US 10,265,639 B2
(45) Date of Patent: Apr. 23, 2019

(54) PROCESS FOR PRODUCING ACETIC ACID

(71) Applicant: Daicel Corporation, Osaka-shi, Osaka (JP)

(72) Inventors: Masahiko Shimizu, Himeji (JP); Yoshihisa Mizutani, Himeji (JP); Hiroyuki Miura, Himeji (JP)

(73) Assignee: Daicel Corporation, Osaka-shi, Osaka (JP)

( * ) Notice: Subject to any disclaimer, the term of this patent is extended or adjusted under 35 U.S.C. 154(b) by 0 days.

(21) Appl. No.: 15/507,137

(22) PCT Filed: Jan. 16, 2017

(86) PCT No.: PCT/JP2017/001213
§ 371 (c)(1),
(2) Date: Feb. 27, 2017

(87) PCT Pub. No.: WO2018/008172
PCT Pub. Date: Jan. 11, 2018

(65) Prior Publication Data
US 2018/0009732 A1 Jan. 11, 2018

Related U.S. Application Data

(60) Provisional application No. 62/359,552, filed on Jul. 7, 2016.

(51) Int. Cl.
*B01D 3/36* (2006.01)
*B01D 3/40* (2006.01)
*B01D 3/42* (2006.01)
*C07C 51/12* (2006.01)
*C07C 51/44* (2006.01)
*B01D 3/14* (2006.01)

(52) U.S. Cl.
CPC ............... *B01D 3/40* (2013.01); *B01D 3/148* (2013.01); *B01D 3/36* (2013.01); *B01D 3/4255* (2013.01); *B01D 3/4261* (2013.01); *C07C 51/12* (2013.01); *C07C 51/44* (2013.01)

(58) Field of Classification Search
CPC ............ C07C 51/44; C07C 51/46; B01D 3/40
See application file for complete search history.

(56) References Cited

U.S. PATENT DOCUMENTS

| | | | | | |
|---|---|---|---|---|---|
| 5,625,095 A | * | 4/1997 | Miura | ..................... | C07C 51/12 562/519 |
| 5,723,660 A | * | 3/1998 | Morimoto | ............ | B01J 31/0231 562/517 |
| 5,756,836 A | * | 5/1998 | Shimizu | .................. | C07C 51/12 562/519 |
| 8,859,810 B2 | * | 10/2014 | Golightly | ................ | C07C 51/12 562/608 |
| 2013/0310603 A1 | | 11/2013 | Shimizu et al. | | |
| 2015/0025270 A1 | | 1/2015 | Shimizu et al. | | |

FOREIGN PATENT DOCUMENTS

| | | | |
|---|---|---|---|
| EP | 2 949 640 A1 | | 12/2015 |
| JP | 8-67650 A | | 3/1996 |
| JP | 09-040590 A | | 2/1997 |
| JP | 9-040590 A | * | 10/1997 |
| WO | WO-2012/081416 A1 | * | 6/2012 |
| WO | WO-2013/137236 A1 | * | 9/2013 |
| WO | WO 2014/031407 A1 | | 2/2014 |
| WO | WO 2016/194850 A1 | | 12/2016 |

OTHER PUBLICATIONS

Seader et al, Perry's Chemical Engineering Handbook, 7th Edition, 1997, Distillation, McGraw Hill, New York, pp. 1-108. (Year: 1997).*
Wikipedia (Wikipedia, Azeotropes, pp. 1-7, recovered from https://en.wikipedia.org/wiki/Azeotrope_tables on Jul. 3, 2018. (Year: 2018).*
International Search Report for Application No. PCT/JP2017/001213, dated Apr. 18, 2017.
Written Opinion for Application No. PCT/JP2017/001213, dated Apr. 18, 2017.
Extended European Search Report for Application No. 17706400.3, dated Jan. 4, 2018.

* cited by examiner

*Primary Examiner* — Paul A Zucker
(74) *Attorney, Agent, or Firm* — Birch, Stewart, Kolasch & Birch, LLP

(57) ABSTRACT

A process for separating or removing permanganate reducing compounds (PRC's) from a first mixture containing at least one PRC, methyl iodide, and water comprises the steps of: feeding the first mixture to a feed port of a distillation column, and distilling and separating the first mixture into an upper stream and a lower stream, wherein the distillation of the first mixture forms a second mixture at an upper position than the feed port, and the process further comprises the steps of: withdrawing the second mixture as the upper stream, and withdrawing the lower stream from a lower position than the feed port.

11 Claims, 5 Drawing Sheets

[Fig. 1]
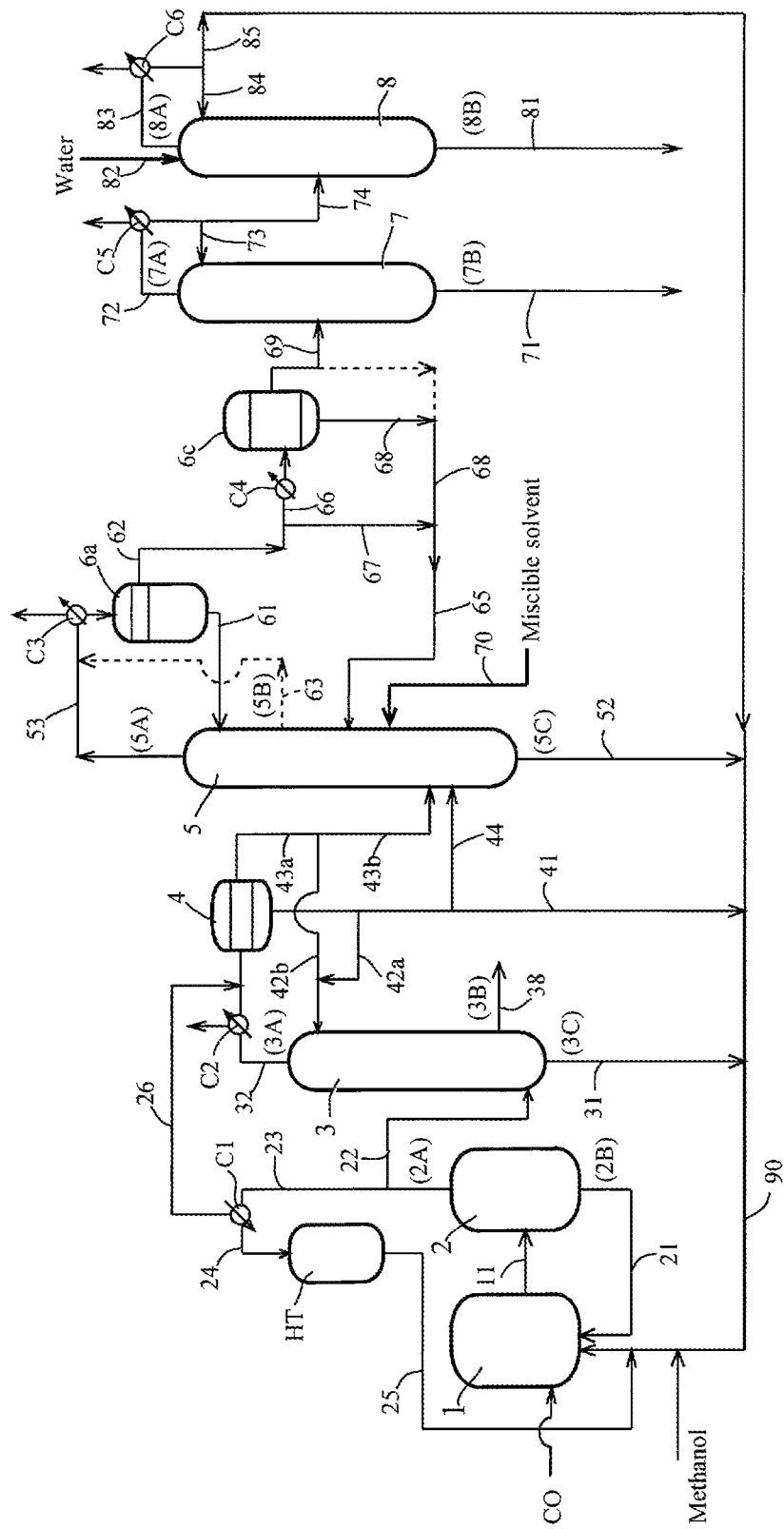

[Fig. 2]
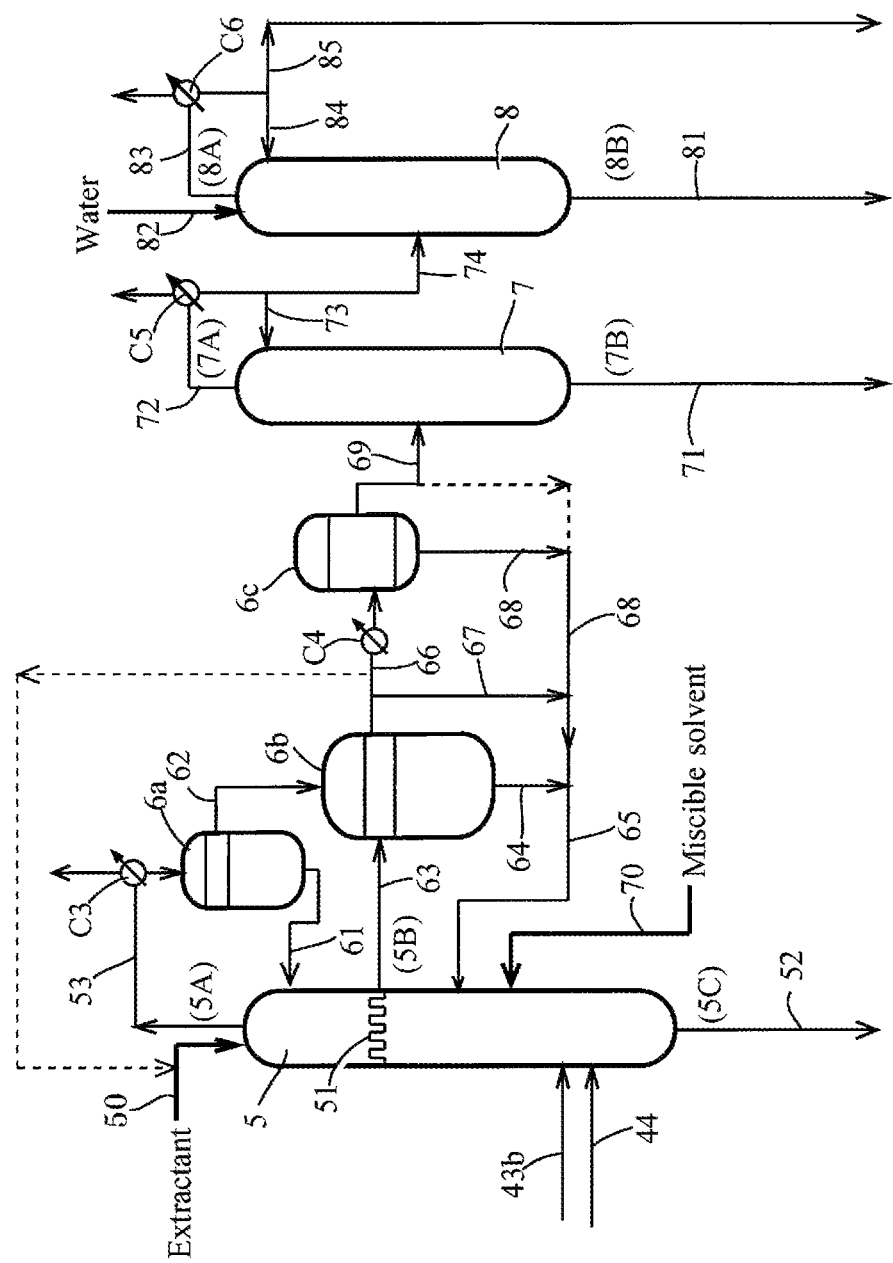

[Fig. 3]
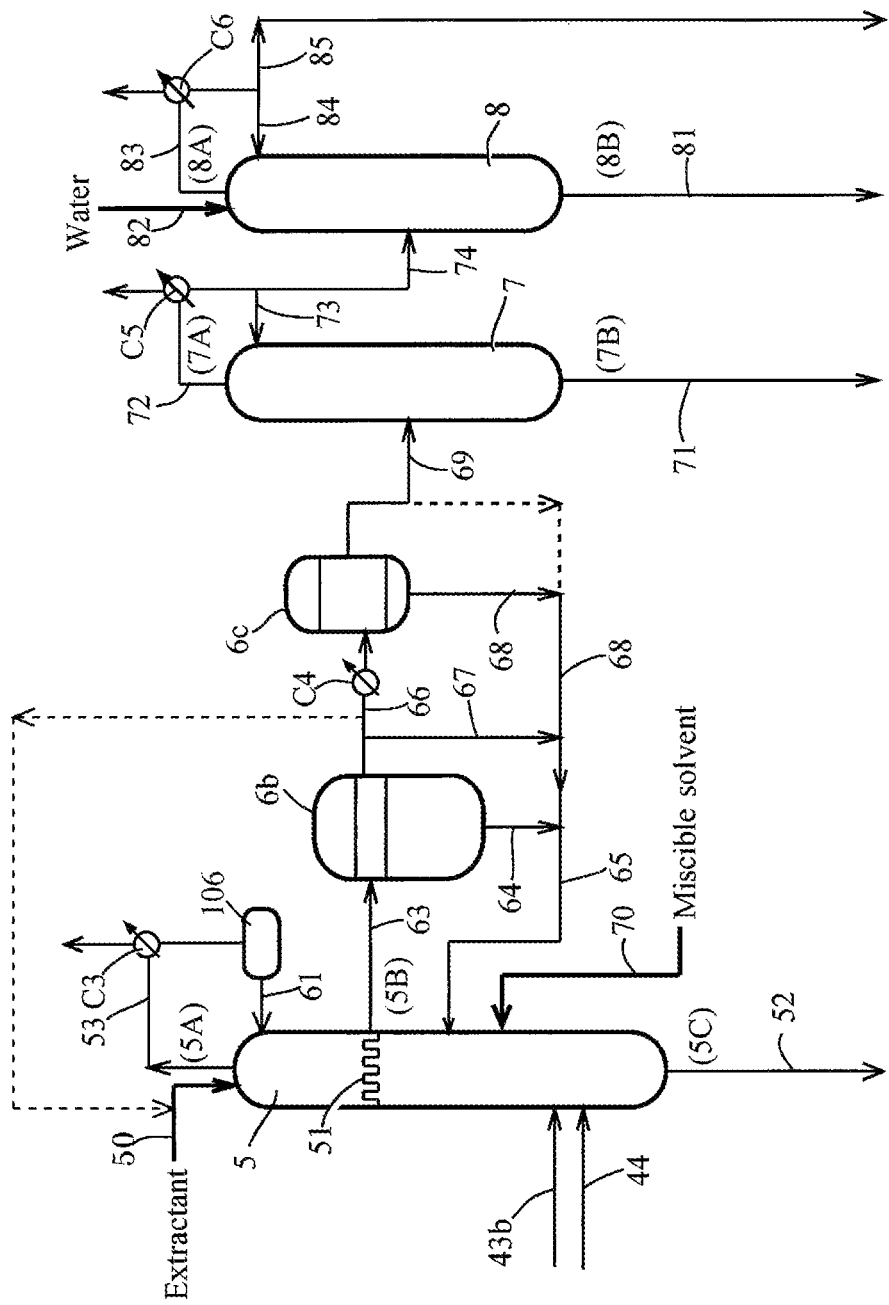

[Fig. 4]
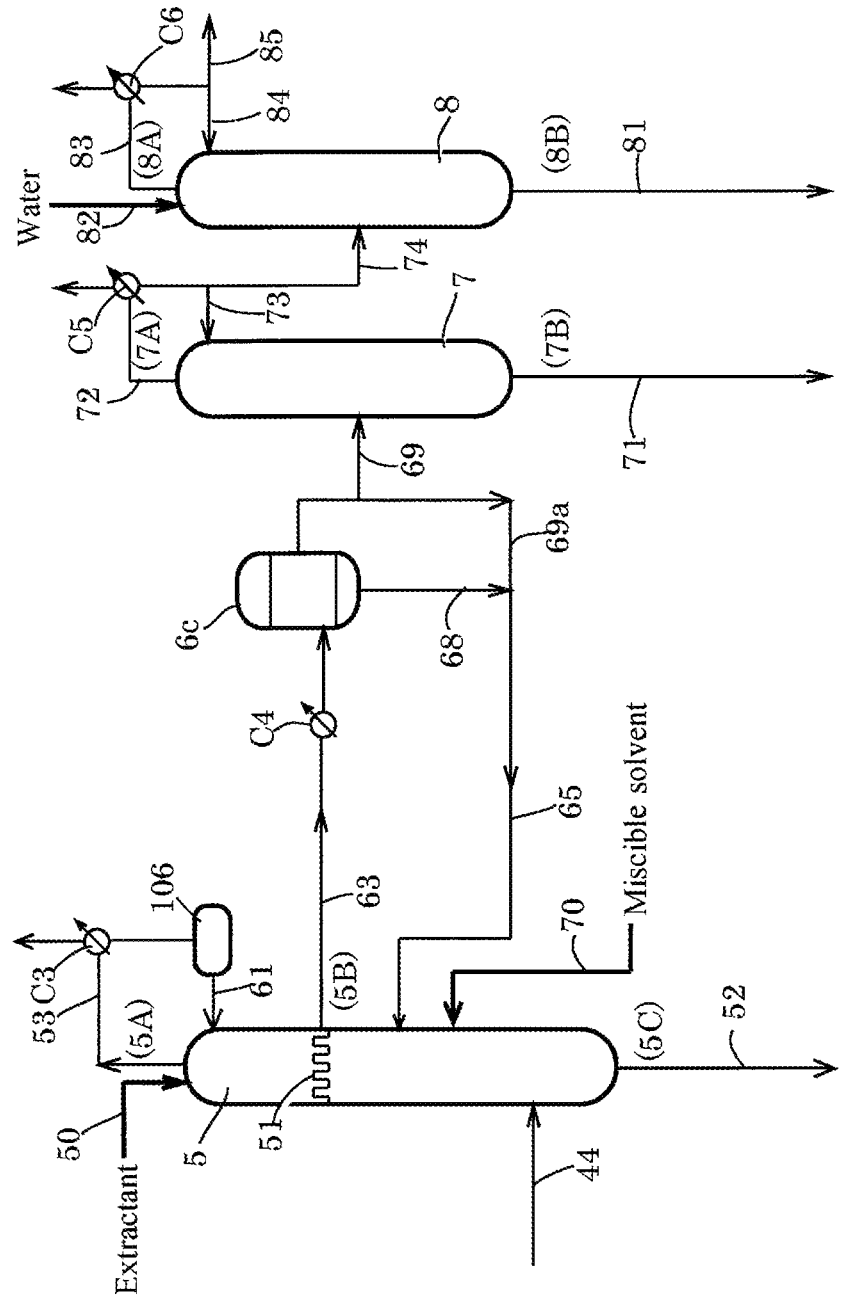

[Fig. 5]
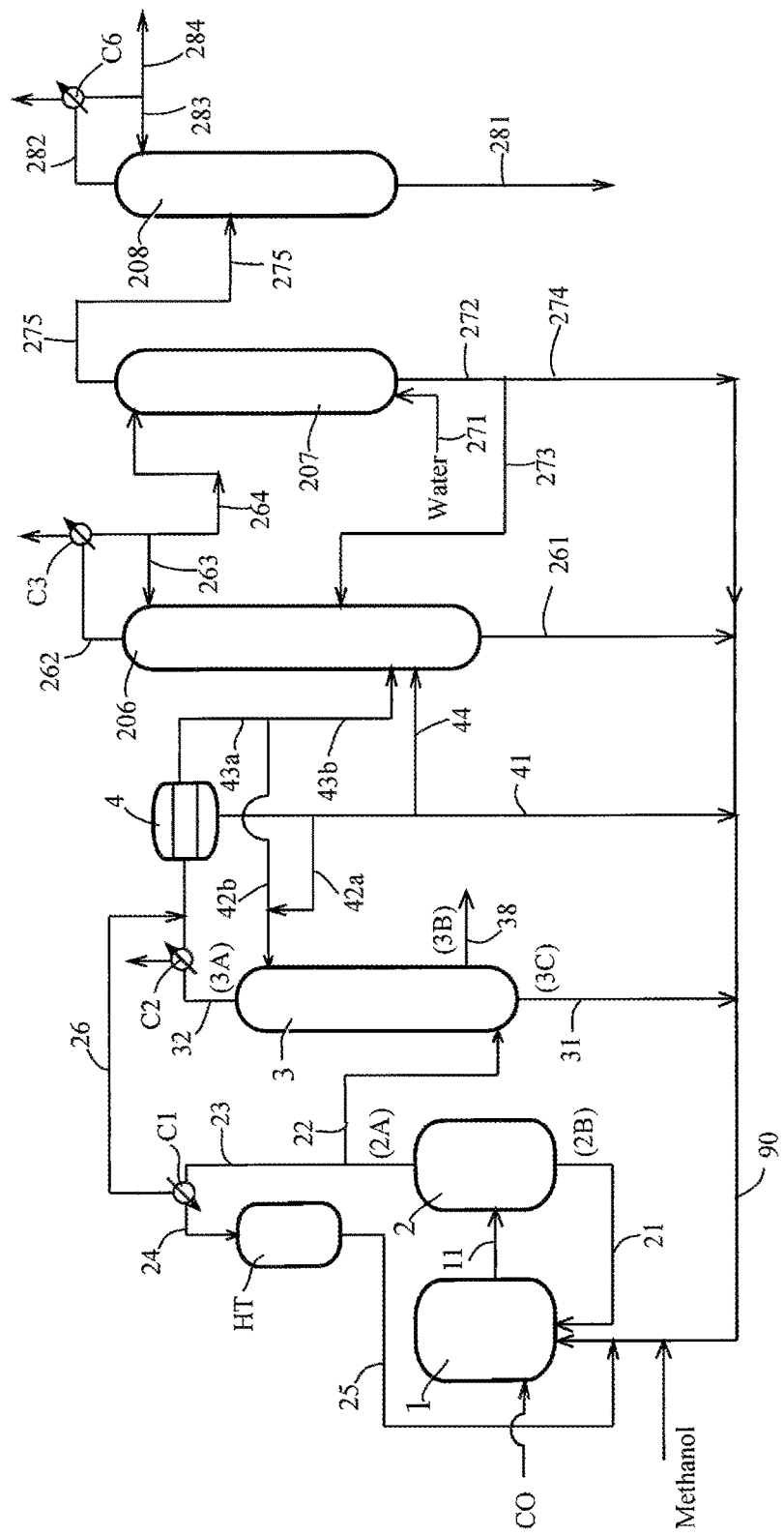

PROCESS FOR PRODUCING ACETIC ACID

TECHNICAL FIELD

The present invention relates to processes useful for separating permanganate reducing compounds (PRC's) such as acetaldehyde and methyl iodide from each other to remove the PRC's, and also relates to processes for producing acetic acid by methanol carbonylation with utilizing the above separation processes.

BACKGROUND ART

Acetic acid is produced industrially by carbonylating methanol in the presence of water, a rhodium catalyst, a metal iodide, and methyl iodide. For the methanol carbonylation reaction, the reaction mixture contains small amounts of by-products (impurities), for example, a carbonyl compound (e.g., acetaldehyde, butyraldehyde, crotonaldehyde, 2-ethylcrotonaldehyde, and an aldol condensation product thereof), an organic iodide (e.g., a $C_{2-12}$alkyl iodide such as ethyl iodide, butyl iodide, or hexyl iodide), and others. These impurities result in low quality of acetic acid. For example, a permanganate reducing compound test (permanganate time) detects extremely small amounts of impurities (permanganate reducing compounds; PRC's) even if the extremely small amounts are difficult to determine quantitatively by current advanced instrumental analysis. Unfortunately, acetaldehyde and methyl iodide have close boiling points to each other, and thus it is difficult to separate acetaldehyde and methyl iodide from each other efficiently by an ordinary distillation means alone.

Japanese Patent Application Laid-Open Publication No. 8-67650 (JP-8-67650A, PTL1) discloses a process for removing acetaldehyde, comprising the steps of: separating a reaction mixture of methanol carbonylation into a volatile phase containing acetic acid, methyl acetate and methyl iodide and a less-volatile phase containing a rhodium catalyst; distilling the volatile phase to form a product mixture containing acetic acid and an overhead containing methyl acetate and methyl iodide; separating the overhead into a lower phase (methyl iodide phase) and an upper phase (an aqueous phase containing acetaldehyde); distilling the lower phase and/or the upper phase in a distillation column (acetaldehyde removing column) to form an acetaldehyde concentrate from a top of the column; and subjecting the acetaldehyde concentrate to a water extraction.

According to this process, for coexistence of methyl acetate with PRC's as well as methyl iodide, methyl acetate is dissolved in and distributed to an aqueous phase in the water extraction, and thus methyl iodide may also undesirably be extracted into the aqueous phase. This results in a loss of methyl iodide. Moreover, this process requires a step of adding water to the acetaldehyde concentrate for the water extraction.

Further, in distilling the upper phase (aqueous phase) containing acetaldehyde, it is necessary to provide a large amount of energy for distillation and separation of acetaldehyde due to distillation of water having a large latent heat for evaporation, or it is necessary to reduce the amount of energy required for the distillation by increasing the number of distillation plates. Whereas, in distilling the lower phase (methyl iodide phase), it is necessary to increase a reflux amount or to increase the number of distillation plates, due to a small difference in boiling point between methyl iodide and acetaldehyde. Moreover, the distillation of a mixture or homogeneous liquid of the upper phase and the lower phase also involves an increase in the amount of vapor (the amount of heat energy) in the distillation column and/or an increase in the number of distillation plates. This results in economically low production of acetic acid.

Furthermore, this process fails to increase an acetaldehyde removal efficiency in the distillation column, because acetaldehyde is not concentrated in the overhead effectively.

WO 2014/031407 (PTL 2) discloses a process for producing acetic acid, the process comprising the steps of: separating a crude acetic acid composition in a light ends column (a splitter column) into an overhead stream comprising methyl iodide, water, methyl acetate, and permanganate reducing compounds (PRC's), and an acetic acid product stream; separating a portion of the overhead stream in a first distillation column to form a stream enriched in at least one PRC, wherein the enriched stream further comprises at least some of the methyl iodide; and extractive distilling the enriched stream with an extractive agent (e.g., water) in a second distillation column to form a distillate comprising methyl iodide and a residue comprising at least one PRC and optionally less than 1 wt. % methyl iodide. This document also discloses a mass flow ratio of the enriched stream relative to the extractive agent of at least 0.01:1. Examples of this document disclose the mass flow ratio of the enriched stream relative to the extractive agent of 4:1.

According to this process, after the concentration of the PRC in the first distillation column, the extractive distillation with the extractive agent (e.g., water) in the second distillation column is carried out to obtain an aqueous phase containing the PRC which is then withdrawn for removal of the PRC. Thus, this process requires an additional second distillation step, and the process needs additional equipment or facilities, increasing costs, and complicates the operation of the process.

Furthermore, according to this process, for distillation and separation in the first distillation column, as the same as the process described in PTL 1, it is necessary to provide a large amount of energy or it is necessary to increase the number of distillation plates. In addition, the extractive distillation of the PRC's in the second distillation column needs a large amount of an extractive agent and a large number of the distillation plates and thus requires a large amount of separation energy. Further, methyl acetate or acetic acid coexistent with the PRC's in the second extractive distillation step is dissolved in an aqueous phase in the water extractive distillation, and thus methyl iodide may undesirably be extracted into the aqueous phase. This results in a loss of methyl iodide.

CITATION LIST

Patent Literature

PTL 1: JP-8-67650A (Claims, [0007], [100181], and Examples)
PTL 2: WO 2014/031407 (Claims and [0064])

SUMMARY OF INVENTION

Technical Problem

It is therefore an object of the present invention to provide a process for efficiently separating PRC's and methyl iodide from each other, and a process for producing acetic acid.

Another object of the present invention is to provide a process for effectively separating PRC's, which result in low quality of acetic acid, and methyl iodide from each other with a low energy without any additional step such as addition of water or an extractant (or an extraction solvent), and a process for producing acetic acid.

It is still another object of the present invention to provide a process for efficiently separating PRC's and methyl iodide from each other without water extraction or water extractive distillation, and a process for producing acetic acid.

It is a further object of the present invention to provide a process for efficiently separating PRC's and methyl iodide from each other even in the coexistence of methyl acetate and/or acetic acid, and a process for producing acetic acid.

Solution to Problem

The inventors of the present invention made intensive studies to achieve the above objects and finally found that (i) distillation of a first mixture containing methyl iodide, and acetaldehyde having a low concentration in the coexistence of water allows at least a portion of water in the first mixture to rise (or be transferred) to an upper position (or an upper height level) than a feed port [specifically, the water in the first mixture is transferred (or moved) to an upper stream predominantly than a bottom stream or lower stream] to form a second mixture containing the portion of water (for example, an azeotropic mixture containing water); and (ii) acetaldehyde is removed by withdrawing the second mixture as an overhead stream and/or a side-cut stream (hereinafter, the overhead stream and/or the side-cut stream may be referred to as an upper stream) to form an organic phase rich in methyl iodide and an aqueous phase rich in acetaldehyde, and withdrawing the aqueous phase. The present invention was accomplished based on the above findings.

Hereinafter, the present invention will be explained with respect to reference numerals in the drawings. The reference numerals are used to aid understanding of the present invention and are not intended to be limited to specific units or process streams indicated by the reference numerals. For example, although FIG. 1 shows a process comprising indirectly feeding an overhead stream or a first mixture (3A) from a first distillation column (3) to a second distillation column (5), any stream having a composition of the first mixture (3A) may be fed to any one or plurality of distillation columns following the first distillation column (3); any one or plurality of distillation columns is not limited to the second distillation column (5).

That is, one aspect of the present invention provides a process for separating or removing permanganate reducing compound (PRC's) (in particular, at least acetaldehyde) from a first mixture (3A) containing at least one PRC (a PRC such as acetaldehyde), methyl iodide, and water. The process comprises feeding the first mixture (3A) to a feed port of a first distillation column, and distilling the first mixture (3A) in a distillation step (5) to separate the first mixture (3A) into an upper stream and a lower stream (5C). The upper stream may contain an overhead stream (5A) and/or a side-cut stream (5B). The distillation of the first mixture (3A) forms a second mixture at an upper position than the feed port. The second mixture is withdrawn as the upper stream (5A)(5B), and the lower stream is withdrawn from a position lower than the feed port, and thus the PRC's are separated or removed from the first mixture (3A).

The distillation of the first mixture (3A) may allow at least a portion of water in the first mixture (3A) to rise (or move upward) to an upper position than the feed port, forming a second mixture containing the portion of water, the second mixture may be withdrawn as the upper stream (5A)(5B), and the lower stream having a water content lower than the first mixture may be withdrawn from a position lower than the feed port, and thus the PRC's may be separated or removed from the first mixture (3A).

According to the process, the water in the first mixture (3A) is transferred to the upper stream (5A)(5B) predominantly than the lower stream (5C), the upper stream is withdrawn to separate the upper stream into an aqueous phase and an organic phase, and the aqueous phase is withdrawn and removed. Therefore methyl iodide and PRC's can efficiently be separated from each other, without water extraction or water extractive distillation, by a small number of steps with a small amount of energy. As used herein, the expression "water is transferred to an upper stream predominantly" means the following: for example, assuming that the water ("1") in a first mixture (containing, for example, water, acetaldehyde, methyl iodide, methyl acetate, or others) is transferred or distributed to an original upper stream and an original lower stream at a ratio of "0.01" and "0.99", respectively, according to an original vapor-liquid equilibrium of the mixture in which water does not form an azeotrope with other components, the water is transferred or distributed to an upper stream and a lower stream at a ratio of "more than 0.01" and "less than 0.99", respectively, by distillation (for example, by formation of an azeotropic mixture due to distillation). Thus, the upper stream has a water content higher than the original upper stream of the first mixture, and the lower stream has a water content lower than the original lower stream of the first mixture. The upper stream is efficiently separable into an aqueous phase and an organic phase.

In another aspect of the present invention, water in the first mixture (3A) is transferred to the upper stream (5A)(5B) predominantly than the lower stream (5C). Not less than 1% by weight (e.g., not less than 5% by weight, preferably not less than 10% by weight, and more preferably not less than 50% by weight) of water in the first mixture (3A) may be transferred or distributed to the upper stream (5A)(5B). Not more than 99% by weight (e.g., not more than 95% by weight, preferably not more than 90% by weight, and more preferably not more than 50% by weight) of water in the first mixture (3A) may be transferred or distributed to the lower stream (5C). The lower stream may have a ratio ($H_2O$/MeI) of water ($H_2O$) relative to methyl iodide (MeI) lower than the first mixture. The upper stream may have a ratio ($H_2O$/MeI) of water ($H_2O$) relative to methyl iodide (MeI) higher than the first mixture.

The first mixture (3A) may contain acetaldehyde, methyl iodide, and water and may further contain the following (a) and/or (b): (a) methyl acetate, (b) at least one member selected from the group consisting of acetic acid, methanol, dimethyl ether, and an acetaldehyde derivative (a derivative from acetaldehyde). The first mixture (3A) may contain 10 ppm to 30% by weight acetaldehyde, 0.1 to 90% by weight methyl iodide, and 0.1 to 90% by weight water. The first mixture (3A) may further contain 1 to 30% by weight methyl acetate. The total amount of the first mixture, including an impurity or impurities, is 100% by weight. The first mixture (3A) may be separated into two phases, and the first mixture (3A) may contain at least a portion of an organic phase, at least a portion of an aqueous phase, or a mixture of the organic phase with the aqueous phase.

According to a further aspect of the present invention, the upper stream (5A)(5B) and the lower stream (5C) may be separated without supply of water to the distillation column. The distillation of the first mixture may form a concentration zone of PRC's and methyl iodide at an upper position than the feed port of the distillation column and allows at least a portion of water in the first mixture to rise (or move upward) to the concentration zone; and a stream or fluid of the concentration zone may be withdrawn as an upper stream. In this process, a mixture falling from the concentration zone may be withdrawn as a side-cut stream. Alternatively, water may be added to a concentration zone in which PRC's and methyl iodide are concentrated in the distillation column, the extraction mixture falling from the concentration zone may be withdrawn as a side-cut stream, and water in the first mixture may be transferred to the upper stream predominantly. As a position for feeding water to the column, a position below a side-cut port or plate may be selected.

Further, the upper stream (5A)(5B) may be separated into an organic phase containing at least methyl iodide and an aqueous phase, and the organic phase and/or the aqueous phase may be recycled to the distillation step (5) by the following method (a), (b), or (c):

(a) withdrawing the upper stream (5A)(5B) from the distillation column (5), separating the withdrawn upper stream into an aqueous phase containing at least acetaldehyde and an organic phase containing methyl iodide, and recycling the organic phase and/or the aqueous phase to the distillation column (5), (b) withdrawing the upper stream (5A)(5B) from the distillation column (5), separating the withdrawn upper stream into an aqueous phase containing at least acetaldehyde and an organic phase containing methyl iodide, and recycling at least a portion of the aqueous phase and the organic phase to the distillation column (5), (c) separating the upper stream (5A)(5B) into an aqueous phase and an organic phase containing at least methyl iodide, subjecting at least a portion of the aqueous phase to distillation in a succeeding third distillation step (7) and/or water extractive distillation in a succeeding fourth distillation step (8), and directly or indirectly recycling the organic phase to the distillation column (5).

Further, the process may comprise the steps of: separating the upper stream (5A)(5B) into an aqueous phase and an organic phase; distilling at least a portion of the aqueous phase in a succeeding third distillation step (7); directly or indirectly recycling the organic phase to the second distillation step (5); and directly or indirectly feeding at least one miscible solvent to the second distillation step (5), wherein the miscible solvent is miscible with the organic phase separated from the upper stream (5A)(5B) and is selected from the group consisting of water, acetic acid, methyl iodide, and methanol.

In a further aspect of the present invention, the process may comprise: a reaction step of continuously carbonylating methanol in the presence of a catalyst system comprising a metal catalyst, a metal halide, and methyl iodide; a flash evaporation step of continuously separating the reaction mixture into a volatile phase (or volatile fraction) and a less-volatile phase (or low-volatile phase or less-volatile fraction), the volatile phase containing product acetic acid and methyl iodide, and the less-volatile phase containing the metal catalyst and the metal halide; a distillation step of continuously separating the volatile phase into an overhead containing methyl iodide and by-product acetaldehyde, and a stream containing acetic acid; and a biphasic separation step of condensing a gaseous phase to form two phases (an aqueous phase and an organic phase), the gaseous phase being produced from at least one of the above steps and containing at least acetaldehyde and methyl iodide. At least a portion of the aqueous phase and/or the organic phase produced in such a biphasic separation step may be subjected to the distillation column to provide an upper stream.

A further aspect of the present invention provides a process for producing acetic acid utilizing the separation process. The process for producing acetic acid comprises the steps of: distilling a mixture (2A) containing at least one permanganate reducing compound (PRC), methyl iodide, water, methyl acetate, and acetic acid to separate the mixture into an overhead (3A) containing at least one PRC, methyl iodide and water, and an acetic acid stream (3B) containing product acetic acid; distilling at least a portion of the overhead (3A) in the distillation column (5) to form an upper stream and a lower stream; withdrawing the upper stream; biphasically separating the withdrawn upper stream into an aqueous phase and an organic phase; withdrawing the aqueous phase: and withdrawing the lower stream from a lower position than the feed port. The upper stream may be an overhead stream and/or a side-cut stream. The lower stream may have a content rate and an amount of water lower than those of water in the overhead.

Specifically, acetic acid may be produced continuously by a process comprising the steps of: (1) a reaction step of continuously carbonylating methanol in the presence of a catalyst system comprising a metal catalyst, a metal halide, and methyl iodide; (2) a flash evaporation step of continuously separating the reaction mixture into a volatile phase (2A) and a less-volatile phase (2B), the volatile phase (2A) containing product acetic acid and methyl iodide, and the less-volatile phase (2B) containing the metal catalyst and the metal halide; (3) a distillation step of continuously separating the volatile phase (2A) into an overhead (3A) containing methyl iodide and by-product acetaldehyde and water, and a stream (3B) containing acetic acid; and (5) a distillation step of distilling at least a portion of the overhead (3A) in the distillation column.

As used herein, acetaldehyde may simply be referred to as PRC's. The overhead stream (5A) and/or the side-cut stream (5B) may simply be referred to as an upper stream (5A)(5B). The lower stream (5C) is to be withdrawn from a lower position in a distillation column than a port for withdrawing the upper stream (5A)(5B) and may mean a bottom stream (or column bottom stream). Thus, the lower stream (5C) may also be referred to as a bottom stream accordingly. The distillation of the first mixture allows water in the first mixture to distribute or transfer to an upper stream predominantly than a lower stream, and thus the distillation of the first mixture may simply be referred to as "distributive distillation" or "azeotropic distillation".

Advantageous Effects of Invention

According to the present invention, water in the first mixture is allowed to be transferred to the upper stream predominantly than the lower stream, and an aqueous phase formed by biphasically separating the upper stream is removed to efficiently separate PRC's and methyl iodide from each other. Thus, PRC's and methyl iodide are efficiently separable from each other with a low energy without necessity of water extraction or water extractive distillation. Further, PRC's and methyl iodide are efficiently separable from each other even in the coexistence with methyl acetate or acetic acid.

BRIEF DESCRIPTION OF DRAWINGS

FIG. 1 is a flow diagram for explaining a production process (or production apparatus) of acetic acid in accordance with an embodiment of the present invention.

FIG. 2 is a partial flow diagram for explaining a production process (or production apparatus) of acetic acid in accordance with another embodiment of the present invention.

FIG. 3 is a partial flow diagram for explaining a production process (or production apparatus) of acetic acid in accordance with a further embodiment of the present invention.

FIG. 4 is a partial flow diagram for explaining a production process (or production apparatus) of acetic acid in accordance with a still another embodiment of the present invention.

FIG. 5 is a flow diagram for explaining a conventional production process (or production apparatus) of acetic acid.

DESCRIPTION OF EMBODIMENTS

Hereinafter, the present invention will be explained in detail with reference to the drawings if necessary. In FIGS. 1 to 5, each step and a main apparatus or unit for the corresponding step may be indicated by the same reference numeral. Unless otherwise specifically noted, an acetaldehyde-containing aqueous phase obtainable by liquid-liquid (or biphasic) separation is synonymous with a light phase or an upper phase, and a methyl iodide-containing organic phase obtainable by liquid-liquid (or biphasic) separation is synonymous with a heavy phase, a methyl iodide phase, or a lower phase. An aqueous phase obtainable by extraction is synonymous with an extract, and an organic phase obtainable by extraction means the same as a raffinate.

With reference to a distillation column, the term "number of plates" means either the number of theoretical plates or the number of actual plates. For example, one theoretical plate corresponds to two actual plates if the efficiency of the actual plate is 50%. The species or kind of the distillation column is not limited to a plate (Oldershaw) column, and may be a packed column. The species or kind of the distillation column is not particularly limited to a specific one. Hereinafter, unless otherwise specifically noted, the term "number of plates" simply means the number of actual plates in a plate column. The position at which a fluid flows in/flows out a packed column (inflow/outflow position) means a position corresponding to a height level of a plate of a plate column. For example, the 20th plate from the bottom of a plate column having the number of actual plates of 50 means a height level corresponding to the 20th plate/the 50 plates from the bottom of a packed column (the height level "0.4" relative to the height "1" of a packed layer or bed of a packed column).

The embodiment of FIG. 1 shows a continuous process (or apparatus) for producing acetic acid from a reaction mixture (or a liquid reaction medium) produced by carbonylation reaction of methanol with carbon monoxide in the presence of a catalyst system comprising a rhodium catalyst as a metal catalyst and a co-catalyst [lithium iodide as a metal halide and methyl iodide] as well as and acetic acid, methyl acetate, and a finite (or limited) amount of water.

The process (or production apparatus) comprises (1) a reaction step (a reaction system or a reactor) for carrying out a carbonylation reaction of methanol; (2) a flash evaporation step (a flasher) for separating a reaction mixture (or a reaction liquid) containing product acetic acid into a volatile phase (or lower boiling point fraction) (2A) and a less-volatile phase (or higher boiling point fraction) (2B); (3) a first distillation step (a splitter column or a distillation column) for separating the volatile phase (2A) into a first overhead (3A), an acetic acid stream (3B) as a side-cut stream, and a bottom liquid stream (higher boiling point fraction) (3C); (4) a first liquid-liquid separation step for condensing the first overhead (3A) to form two phases; (5) a second distillation step (a second distillation column) for separating an aqueous phase and/or an organic phase (a heavy phase rich in methyl iodide) formed in the liquid-liquid separation step (4) into a second overhead stream (5A) and/or a side-cut stream (5B) [an upper stream (5A) (5B)] and a lower stream or bottom stream (5C); (6) a second liquid-liquid separation step (a separation unit 6a and/or a hold tank 6b as well as a decanter 6c) for separating the second overhead stream (5A) and/or the side-cut stream (5B) into two phases; (7) a third distillation step (a third distillation column) for separating an aqueous phase (light phase) formed in the second liquid-liquid separation step (6) into a third overhead stream (7A) and a liquid stream (7B); and (8) a fourth distillation step (a fourth distillation column) for subjecting the third overhead stream (7A) to water extractive distillation to form an overhead stream (8A) and a bottom liquid stream (8B).

Incidentally, among these steps, the process at least comprises the second distillation step (5) and the second liquid-liquid separation step (6). Other steps [for example, the first liquid-liquid separation step (4), the third distillation step (7), and the fourth distillation step (8)] are not necessarily essential. In some embodiments, the process comprises the first distillation step (3), the liquid-liquid separation step (4), and the second distillation step (5). The second distillation step (5) is not limited to a single distillation step and may contain a plurality of distillation steps using a plurality of distillation columns. For the production of acetic acid, the process usually comprises the reaction step (1) and the flash evaporation step (flasher) (2).

Hereinafter, the process shown in FIG. 1 will be explained in more detail.

(1) Reaction Step (Reactor)

In the reaction step (reactor) (1), methanol and carbon monoxide are continuously fed to a reactor in the presence of a reaction medium containing a carbonylation catalyst system and water and produce acetic acid by carbonylation of methanol.

The carbonylation catalyst system usually contains a metal catalyst (such as a cobalt catalyst, a rhodium catalyst, or an iridium catalyst), a catalyst stabilizer or reaction accelerator, and a co-catalyst. The metal catalysts may be used alone or in combination. The metal catalyst may preferably include a rhodium catalyst and an iridium catalyst (in particular, a rhodium catalyst).

The metal catalyst may be used in the form of a simple metal, a metal oxide (including a complex metal oxide), a metal hydroxide, a metal iodide, a metal carboxylate (e.g., an acetate), a metal salt of an inorganic acid (e.g., a sulfate, a nitrate, and a phosphate), or a metal complex. It is preferred to use the metal catalyst in a form (e.g., a complex form) dissolvable in a liquid phase (or a reaction liquid). The rhodium catalyst may preferably include, for example, a rhodium iodide complex {e.g., $RhI_3$, $[RhI_2(CO)_4]^-$, and $[Rh(CO)_2I_2]^-$} and a rhodium carbonyl complex. The metal catalyst has a concentration of, for example, about 100 to 5000 ppm (on the basis of weight, the same applies hereinafter), preferably about 200 to 3000 ppm, more preferably about 300 to 2000 ppm, and particularly about 500 to 1500 ppm in the whole liquid phase in the reactor.

The catalyst stabilizer or reaction accelerator may include a metal iodide capable of producing an iodide ion in the reaction medium, for example, an alkali metal iodide (e.g., lithium iodide, sodium iodide, and potassium iodide).

Among these stabilizers, lithium iodide is preferred. These co-catalysts or accelerators may be used alone or in combination.

The catalyst stabilizer or reaction accelerator in the whole liquid phase in the reactor has a concentration of, for example, about 1 to 25% by weight, preferably about 2 to 22% by weight, and more preferably about 3 to 20% by weight. The iodide ion in the reaction system may have a concentration of, for example, about 0.05 to 2.5 mol/L and preferably about 0.25 to 1.5 mol/L.

As the co-catalyst, methyl iodide may be used. The methyl iodide in the whole liquid phase in the reactor has a concentration of, for example, about 1 to 30% by weight, preferably about 5 to 25% by weight, and more preferably about 6 to 20% by weight (e.g., about 8 to 18% by weight).

A preferred carbonylation catalyst system may comprise a rhodium catalyst, a metal iodide as a catalyst stabilizer (e.g., lithium iodide), and methyl iodide as a co-catalyst. To the reactor may be fed a catalyst mixture (a catalyst liquid) containing the carbonylation catalyst system and water.

The reaction medium (or liquid phase) usually contains product acetic acid, methyl acetate formed by a reaction of product acetic acid and raw material methanol, and water. The acetic acid also plays as a solvent. Moreover, the reaction medium (or the liquid phase) usually contains unreacted raw material methanol. The proportion of methyl acetate in the whole reaction liquid may be about 0.1 to 30% by weight, preferably about 0.3 to 20% by weight, and more preferably about 0.5 to 10% by weight (e.g., about 0.5 to 6% by weight). The water in the reaction medium may have a low concentration. The water in the whole reaction liquid has a concentration of, for example, about 0.1 to 15% by weight, preferably about 0.5 to 10% by weight, and more preferably about 0.8 to 5% by weight (e.g., about 1 to 3% by weight) and may usually be about 1 to 10% by weight (e.g., about 2 to 5% by weight).

The carbon monoxide partial pressure in the reactor may be a pressure of, for example, about 2 to 30 atmospheres and preferably about 4 to 15 atmospheres. A waste gas containing carbon monoxide produced in the succeeding step(s) may be recycled to the reaction system.

The carbonylation reaction produces hydrogen by a reaction of carbon monoxide with water. Hydrogen increases the catalyst activity. Thus hydrogen may be fed to the reactor if necessary. Hydrogen may be fed to the reactor by recycling gaseous component(s) (including hydrogen, carbon monoxide, or other gases) exhausted in the process, if necessary after purifying and/or separating the gaseous component(s) in the succeeding step(s). The hydrogen partial pressure in the reaction system may be a pressure of, for example, about 0.5 to 250 kPa (e.g., about 1 to 200 kPa), preferably about 5 to 150 kPa, and more preferably about 10 to 100 kPa (e.g., about 10 to 50 kPa) in terms of absolute pressure.

The temperature of the carbonylation reaction may be, for example, about 150 to 250° C., preferably about 160 to 230° C., and more preferably about 170 to 220° C. The reaction pressure (total reactor pressure), including partial pressures of by-products, may be, for example, about 15 to 40 atmospheres.

In the reactor, the carbonylation reaction of methanol proceeds with forming an equilibrium between a liquid-phase reaction system and a gaseous-phase system. The liquid-phase reaction system contains the reactant(s) and the metal catalyst component, and the gaseous-phase system comprises carbon monoxide, reaction products (hydrogen, methane, and carbon dioxide), and vaporized lower boiling point components (e.g., methyl iodide, product acetic acid, and methyl acetate). The vapor components (vent gas) may be withdrawn from the top (or head) of the reactor (1), or may be subjected to an absorption treatment to recover carbon monoxide and/or hydrogen which may be then recycled to the reactor.

The reaction mixture (the crude reaction liquid) contains acetic acid, lower boiling point components or impurities, each having a boiling point lower than acetic acid (e.g., methyl iodide as a co-catalyst, methyl acetate as a reaction product of acetic acid and methanol, water, and acetaldehyde as a by-product), and higher boiling point components or impurities, each having a boiling point higher than acetic acid [e.g., a metal catalyst component (e.g., a rhodium catalyst), lithium iodide as a catalyst stabilizer, and a $C_{3-12}$alkanecarboxylic acid (e.g., propionic acid)]. Further, by-products derived from acetaldehyde (acetaldehyde derivatives) are also produced. The acetaldehyde derivatives may include, for example, other aldehydes such as butyraldehyde, crotonaldehyde, 2-ethylcrotonaldehyde, and 2-ethylbutyraldehyde; a ketone such as acetone or methyl ethyl ketone; an aldol condensation product thereof; and a $C_{2-12}$alkyl iodide such as ethyl iodide, propyl iodide, butyl iodide, pentyl iodide, or hexyl iodide. The by-products may also include a 3-hydroxyalkanal (e.g., 3-hydroxybutanal); formic acid or the $C_{3-12}$alkanecarboxylic acid (such as propionic acid, butanoic acid, hexanoic acid, heptanoic acid, or octanoic acid); a $C_{3-12}$alkyl alcohol such as butyl alcohol or 2-ethylbutyl alcohol; an ester of methanol or the above alkyl alcohol with acetic acid or the above carboxylic acid; an ether of methanol and/or the above alkyl alcohol (a dialkyl ether such as dimethyl ether); and methane and a hydrocarbon with two or more carbon atoms (e.g., a $C_{2-12}$alkane). These by-products are usually increased in proportion to the square to the cube of the concentration of acetaldehyde. Acetaldehyde and the by-products derived from acetaldehyde (for example, other aldehydes, the ketone, and the aldol condensation product) belong to permanganate reducing compounds (PRC's). Thus, it is preferred to separate and remove acetaldehyde, which is a main by-product, from the reaction mixture and/or the process stream(s) and to recover useful components (e.g., methyl iodide) from the process stream(s) for effective utilization. Incidentally, although the $C_{2-12}$alkyl iodide, including methyl iodide, also belongs to the PRC's, methyl iodide is excluded from the PRC's in the process of the embodiments.

According to one embodiment of the present invention, acetaldehyde is efficiently separable and removable to decrease the concentration of acetaldehyde in the reactor even in a continuous reaction. With the decrease in acetaldehyde concentration or the elimination of acetaldehyde, production of by-products derived from acetaldehyde is significantly prevented. For example, the whole liquid phase in the reactor may have an acetaldehyde concentration of, for example, not more than 1000 ppm (e.g., 0 or detection limit to 700 ppm), preferably not more than 400 ppm (e.g., 5 to 300 ppm), and more preferably about 10 to 250 ppm throughout the whole process.

The space time yield of the objective carboxylic acid (acetic acid) in the reaction system may be, for example, about 5 mol/Lh to 50 mol/Lh, preferably about 8 mol/Lh to 40 mol/Lh, and more preferably about 10 mol/Lh to 30 mol/Lh.

The reaction system is an exothermic reaction system that accompanies heat generation, and the reaction temperature may be controlled (or regulated) by recycling of the condensate which has been cooled or from which heat has been removed, installation of a heat-removable (or heat-removing) unit or a cooling unit (e.g., a jacket), or other means. In order to remove part of the reaction heat, a vapor (vent gas) from the reactor may be cooled in a condenser, a heat exchanger, or other means to separate the vapor into liquid components and gaseous components, and the liquid components and/or the gaseous components may be recycled to the reactor.

(2) Flash Evaporation Step

In the flash evaporation step (2), a portion of the reaction mixture is continuously withdrawn from the reactor 1 and is introduced or fed to a flasher (catalyst separation unit) (2) via a feed line 11 to separate the reaction mixture into a volatile phase (2A) and a less-volatile (2B); the volatile phase (2A) contains product acetic acid, methyl iodide, acetaldehyde, methyl acetate, water, or other compounds, and the less-volatile phase (2B) contains the rhodium catalyst and lithium iodide. At least a first portion of the volatile phase (2A) is fed to a distillation column of the first distillation step (3) via a feed line 22, and the less-volatile phase (2B) is recycled to the reactor of the reaction step (1) via a recycle line 21.

A second portion of the volatile phase (2A) may be cooled and condensed in a condenser C1 on a line 23. The resulting condensate may be held in a hold tank HT for recycling the condensate to the reaction step (reactor) (1). The cooled product (condensate and/or noncondensable component) in the condenser C1 may be fed to the liquid-liquid separation step (4) via a line 26 and may be held in a decanter (4) together with an overhead (3A) from the first distillation step (splitter column) (3), and a mixture of the cooled product and the overhead (3A) may be separated into two phases in the decanter (4).

(Condensation of Volatile Phase)

The second portion of the volatile phase (2A) may be fed, without condensation, to the second distillation step (5) directly or indirectly via the liquid-liquid separation step (4), or may be cooled and condensed in one or a plurality of condensers C1 to form two phases (an aqueous phase and an organic phase) for subjecting the aqueous phase or the organic phase (at least the aqueous phase) to the second distillation step (5) directly or indirectly via the liquid-liquid separation step (4). For example, the second portion of the volatile phase (2A) may optionally be condensed as described above (and optionally be liquid-liquid separated) and mix with the condensate obtained in the liquid-liquid separation step (4), and the mixture may be subjected to the second distillation step (5).

If necessary, the catalyst component (metal catalyst component) may be separated from the less-volatile phase (2B) by one or a plurality of steps and may be recycled to the reaction step (1).

The flash evaporation may include a thermostatic flash in which the reaction mixture is heated and depressurized, an adiabatic flash in which the reaction mixture is depressurized without heating, or a combination of these flash conditions. By such a flash evaporation, the reaction mixture may be separated into the vapor phase and the liquid phase. For example, the flash evaporation may be carried out at a temperature of the reaction mixture of about 80 to 200° C., a pressure (absolute pressure) of the reaction mixture of about 50 to 1000 kPa (e.g., about 100 to 1000 kPa), preferably about 100 to 500 kPa, and more preferably about 100 to 300 kPa.

(3) First Distillation Step (Splitter Column)

In the first distillation step (splitter column) (3), the volatile phase (2A) is separated into a first overhead (3A), an acetic acid stream (3B), and a bottom stream (3C); the first overhead (3A) (overhead gas, lower boiling point stream or lower boiling point fraction) is withdrawn from a top or upper part of the column via a withdrawing line 32, the acetic acid stream (3B) is side-cut via a line 38 and mainly contains acetic acid, and the bottom stream (3C) (higher boiling point stream or higher boiling point fraction) is withdrawn from a bottom or lower part of the column via a bottom line 31. The proportion of the first overhead stream or overhead (3A) may be about 35 to 50% by weight in the whole volatile phase (2A).

The first overhead stream (3A), which corresponds to a first mixture (3A), contains at least one permanganate reducing compound (PRC), methyl iodide, and water. The PRC contains at least by-product acetaldehyde. The first overhead stream (3A) usually contains methyl acetate and practically contains acetic acid, methanol, water, dimethyl ether, by-products derived from acetaldehyde (e.g., an aldehyde such as crotonaldehyde or butyraldehyde; an acetaldehyde derivative such as a $C_{2-12}$alkyl iodide or a $C_{3-12}$alkanecarboxylic acid; and a $C_{2-12}$alkane).

The acetic acid stream or side-cut stream (3B) is further fed to a purification step by a distillation column or other means (not shown) to remove water or higher boiling point impurities or other impurities from the stream (3B), thus producing purified acetic acid with a high purity. The liquid stream (3C) usually contains at least water and acetic acid and also practically contains methanol, propionic acid, or other compounds. The liquid stream (3C) may contain an entrained metal catalyst component. The liquid stream (3C) may be discharged via the line 31, or a portion or whole of the liquid stream (3C) may be recycled to the reaction step (reactor) (1) via a line 90.

In one embodiment of the present invention, the process can be applied to the first mixture or overhead stream which contains at least one PRC, methyl iodide, and water. The first overhead (3A) may be subjected to the second distillation step (5) in a gaseous form. In a preferred embodiment, the first mixture further contains methyl acetate. In one embodiment of the present invention, the process is effectively applied to the first mixture or overhead stream (3A) which contains a high concentration of at least methyl iodide (in particular, high concentrations of both at least methyl iodide and PRC's). Incidentally, the first mixture or overhead stream (3A) may have an increased water concentration relative to the volatile phase (2A). Thus, as shown in FIG. 1, by a predetermined or preceding step or unit operation [e.g., the distillation step (3), the liquid-liquid separation step (4)], the first mixture (3A) in which methyl iodide is (in particular, both methyl iodide and PRC's are) concentrated is produced. In this embodiment, the first mixture (3A) is condensed and biphasically separated in the liquid-liquid separation step (4), and the resulting organic phase and/or aqueous phase is subjected to the second distillation step (5).

The internal temperature of the distillation column (splitter column) of the first distillation step (3) depends on an internal pressure thereof. At the internal pressure of an atmospheric pressure (1 atm=about 0.1 MPa), the distillation column may have a column top temperature of, for example, about 20 to 100° C. (e.g., about 30 to 80° C.) and preferably about 40 to 70° C. (e.g., about 50 to 60° C.), or may have a column bottom temperature of, for example, about 40 to 120° C. (e.g., about 50 to 100° C.) and preferably about 60 to 90° C. (e.g., about 70 to 85° C.). The distillation column may have a pressure of, for example, about 0.1 to 0.5 MPa, preferably about 0.2 to 0.4 MPa, and more preferably about 0.25 to 0.35 MPa in terms of absolute pressure.

The distillation column may have a theoretical number of plates of, for example, about 2 to 100 (e.g., about 5 to 70) and preferably about 7 to 50 (e.g., about 10 to 30). The reflux ratio of the distillation column may be infinity (wherein the infinity means that all the condensate from the top of the distillation column is recycled to the top of the distillation column) or may be, for example, about 1 to 5000 (e.g., about 10 to 4000) and preferably about 100 to 3000 (e.g., about 500 to 2000).

(4) Condensation/Liquid-Liquid Separation Step

The first overhead (3A) from the first distillation step (splitter column or distillation column) (3) is cooled and condensed in a condenser C2 on a withdrawing line 32, and the condensate is biphasically separable into an aqueous phase rich in acetaldehyde and an organic phase rich in methyl iodide in a decanter (a decanter apparatus, a storage container) (4). A portion of the condensate (the aqueous phase and/or the organic phase) is returned to the splitter column (3) via a reflux line 42 (42a, 42b) for reflux. At least a portion of the aqueous phase is fed to a distillation column of the second distillation step (5), and at least a portion of the organic phase is recycled to the reaction step (1) via a line 41. In the embodiment shown in FIG. 1, a portion of the aqueous phase is returned to the splitter column (3) via the reflux line 42b for reflux, the residual portion of the aqueous phase is fed to the distillation column of the second distillation step (5) via a feed line 43b, a first portion of the organic phase is returned to the splitter column (3) via the reflux line 42a for reflux, and a second portion of the organic phase is fed to the distillation column of the second distillation step (5) via a feed line 44, and the residual portion of the organic phase is recycled to the reaction step (1) via a line 41.

Incidentally, to the distillation column of the second distillation step (5) may be fed at least a portion of the aqueous phase (or the whole aqueous phase) or may be fed at least a portion of the organic phase (or the whole organic phase) or may be fed a mixture of the organic phase and the aqueous phase, as far as the upper stream (5A)(5B) is liquid-liquid (or biphasically) separable. In a preferred embodiment, at least a portion of the organic phase (the organic phase rich in methyl iodide) is usually fed to the distillation column of the second distillation step (5). At least a portion of the aqueous phase may be fed to the distillation column of the second distillation step (5).

In addition to the liquid-liquid separation step (decanter) (4) for temporarily holding or retaining the condensate and biphasically separating the condensate, a buffer tank for temporarily holding (or retaining) the condensate (the separated lower phase or upper phase) in the decanter (4) may optionally be utilized for suppressing the flow rate fluctuation of the process stream.

The condensate (as well as the aqueous phase and the organic phase) may have a temperature of, for example, about 20 to 110° C. (e.g., about 25 to 90° C.) and preferably about 30 to 80° C. (e.g., about 35 to 70° C.).

The distillation of the overhead stream or first mixture (3A) forms the upper stream (5A)(5B), which is liquid-liquid separable. The first mixture (3A) may biphasically be separable. In a case where the first mixture (3A) is biphasically separable, at least a portion of the organic phase, at least a portion of the aqueous phase, or a feed liquid containing the first mixture (the organic phase and the aqueous phase) can be fed to the distillation step (5). Thus, in the first mixture (3A), the concentrations of methyl iodide, each of PRC's (a representative compound of PRC's is acetaldehyde), water, or other compounds can be selected from wide concentration ranges.

Hereinafter, with reference to compositions of process streams, concentrations of typical components (acetaldehyde, methyl iodide, methyl acetate, acetic acid, water, and dimethyl ether) will be described, although the process streams inevitably contain other components (including impurities) as described below. The process streams may include the first mixture (3A) and phases (phasically) separated therefrom, the second overhead stream (5A), the side-cut stream (5B) and phases (phasically) separated therefrom, overhead streams (7A)(8A) or condensates thereof, and bottom liquid streams (7B)(8B). As used herein, each process stream (or each phase), including impurities, has a total amount of 100% by weight on the basis of weight.

The first mixture (3A) may contain typical components in broad-range concentrations according to the state of liquid-liquid separation as described below, for example, may contain acetaldehyde in a concentration of about 10 ppm to 30% by weight (e.g., about 100 ppm to 25% by weight, preferably about 500 ppm to 20% by weight), methyl iodide in a concentration of about 0.1 to 90% by weight (e.g., about 1 to 85% by weight, preferably about 3 to 70% by weight), and water in a concentration of about 0.1 to 90% by weight (e.g., about 0.5 to 80% by weight, preferably about 1 to 70% by weight). Further, the first mixture may contain methyl acetate in a concentration of about 1 to 30% by weight (e.g., about 3 to 25% by weight, preferably about 5 to 20% by weight), acetic acid in a concentration of about 0 to 60% by weight (e.g., about 0.3 to 40% by weight, preferably about 0.5 to 35% by weight), and dimethyl ether in a concentration of about 0 to 1% by weight (e.g., about 1 ppm to 0.5% by weight, preferably about 10 ppm to 0.2% by weight).

The first mixture (3A) (a homogeneous liquid, or a mixture of an aqueous phase and an organic phase) may have an acetaldehyde concentration of, for example, about 10 ppm to 10% by weight (e.g., about 100 ppm to 5% by weight) and preferably about 500 ppm to 1% by weight (e.g., about 0.1 to 0.5% by weight). According to one embodiment of the present invention, small amounts of PRC's (e.g., acetaldehyde) can be separated effectively, and thus each of PRC's (e.g., acetaldehyde) in the first mixture (3A) may have a concentration of about 100 to 5000 ppm (e.g., about 500 to 3000 ppm) and usually about 750 to 2500 ppm (e.g., about 1000 to 2000 ppm). The first mixture (3A) may have a methyl iodide concentration of, for example, about 10 to 85% by weight (e.g., about 25 to 80% by weight) and preferably about 40 to 75% by weight (e.g., about 50 to 70% by weight). The first mixture (3A) may have a methyl acetate concentration of, for example, about 0 to 30% by weight (e.g., about 0.1 to 25% by weight) and preferably about 1 to 20% by weight (e.g., about 5 to 20% by weight), or may have a methyl acetate concentration of about 7 to 17% by weight (e.g., about 10 to 15% by weight). The first mixture (3A) may have an acetic acid concentration of, for example, about 0 to 12% by weight (e.g., about 0.1 to 10% by weight) and preferably about 0.5 to 8% by weight (e.g., about 1 to 7% by weight); or may have an acetic acid concentration of about 1 to 5% by weight (e.g., about 1 to 3% by weight). The first mixture (3A) may have a water concentration of, for example, not less than 1% by weight (e.g., about 5 to 87% by weight), preferably not less than 10% by weight (e.g., about 15 to 85% by weight), and more preferably not less than 20% by weight (e.g., about 30 to 83% by weight); or may have a water concentration of about 5 to 50% by weight (e.g., about 10 to 40% by weight) and preferably about 15 to 35% by weight (e.g., about 17 to 30% by weight). The first mixture (3A) may have a dimethyl ether concentration of, for example, about 0 to 1% by weight (e.g., about 1 ppm to 0.5% by weight) and preferably about 5 ppm to 0.3% by weight (e.g., about 10 to 500 ppm).

In a case where the overhead stream or first mixture (3A) is liquid-liquid separated (or forms an organic phase and an aqueous phase), the organic phase (lines 41, 42a, and 44) may have an acetaldehyde concentration of, for example, about 1 ppm to 10% by weight (e.g., about 100 ppm to 5% by weight) and preferably about 300 ppm to 1% by weight (e.g., about 500 ppm to 0.5% by weight). The organic phase may have a methyl iodide concentration of, for example, about 10 to 95% by weight (e.g., about 30 to 93% by weight) and preferably about 50 to 90% by weight (e.g., about 70 to 90% by weight); or may have a methyl iodide concentration of, for example, not less than 10% by weight (e.g., about 15 to 90% by weight), preferably not less than 20% by weight (e.g., about 25 to 90% by weight), more preferably not less than 30% by weight (e.g., about 30 to 80% by weight), and particularly about 40 to 70% by weight (e.g., about 50 to 65% by weight). The organic phase may have a methyl acetate concentration of, for example, about 1 to 30% by weight (e.g., about 3 to 25% by weight) and preferably about 5 to 20% by weight (e.g., about 7 to 16% by weight). The organic phase of the first mixture (3A) may have an acetic acid concentration of, for example, about 0 to 10% by weight (e.g., about 0.1 to 7% by weight) and preferably about 0.3 to 5% by weight (e.g., about 0.5 to 3% by weight). The organic phase may have a water concentration of, for example, about 0 to 50% by weight (e.g., about 0.01 to 40% by weight), preferably about 0.1 to 30% by weight (e.g., about 0.2 to 20% by weight), and more preferably about 0.5 to 10% by weight (e.g., about 1 to 5% by weight); or may have a water concentration of about 0 to 5% by weight (e.g., about 0.1 to 3% by weight) and preferably about 0.3 to 2% by weight (e.g., about 0.5 to 1.5% by weight). The organic phase may have a dimethyl ether concentration of, for example, about 0 to 1% by weight (e.g., about 1 ppm to 0.5% by weight) and preferably about 5 ppm to 0.3% by weight (e.g., about 10 ppm to 0.1% by weight).

In a case where the overhead stream or first mixture (3A) is liquid-liquid separated (or forms an organic phase and an aqueous phase), the aqueous phase (lines 43a and 43b) may have an acetaldehyde concentration of, for example, about 500 ppm to 30% by weight (e.g., about 1000 ppm to 25% by weight) and preferably about 2000 ppm to 20% by weight (e.g., about 3000 ppm to 15% by weight). The aqueous phase may have a methyl iodide concentration of, for example, about 0.1 to 30% by weight (e.g., about 1 to 25% by weight) and preferably about 3 to 20% by weight (e.g., about 5 to 15% by weight); or may have a methyl iodide concentration of not less than 1.5% by weight (e.g., about 2 to 50% by weight), not less than preferably 2% by weight (e.g., about 3 to 40% by weight), and more preferably not less than 4% by weight (e.g., about 5 to 30% by weight). The aqueous phase may have a methyl acetate concentration of, for example, about 1 to 30% by weight (e.g., about 3 to 25% by weight) and preferably about 5 to 20% by weight (e.g., about 7 to 15% by weight). The aqueous phase may have an acetic acid concentration of, for example, about 5 to 60% by weight (e.g., about 10 to 50% by weight) and preferably about 20 to 40% by weight (e.g., about 25 to 35% by weight). The aqueous phase may have a water concentration of, for example, about 10 to 90% by weight (e.g., about 25 to 80% by weight) and preferably about 30 to 75% by weight (e.g., about 40 to 70% by weight). The aqueous phase may have a dimethyl ether concentration of, for example, about 0 to 1% by weight (e.g., about 1 ppm to 0.8% by weight) and preferably about 5 ppm to 0.5% by weight (e.g., about 10 to 2000 ppm).

Incidentally, in a case where the first mixture is a homogeneous liquid or a mixture of an aqueous phase and an organic phase, each component in the homogeneous liquid or the mixture usually has a concentration within the range of the corresponding component in the organic phase and the aqueous phase. In a case where the first mixture is not liquid-liquid separated or the first mixture is a mixture of an organic phase and an aqueous phase, the concentration of each component in the first mixture is a concentration within the maximum and the minimum ranges of the corresponding component of both phases.

The acetic acid stream or side-cut stream (3B) may have a concentration of each of PRC's (typically, acetaldehyde) of, for example, about 0 to 2000 ppm (e.g., about 0 to 1000 ppm), preferably about 0 to 500 ppm (e.g., about 1 to 100 ppm), and more preferably about 0 to 50 ppm or may have the PRC concentration substantially not more than detection or measurable limit. The acetic acid stream (3B) may have a methyl iodide concentration of, for example, about 0 to 15% by weight (e.g., about 0.3 to 10% by weight) and preferably about 0.5 to 7% by weight (e.g., about 1 to 5% by weight). The acetic acid stream (3B) may have a methyl acetate concentration of, for example, about 0 to 15% by weight (e.g., about 0.3 to 10% by weight) and preferably about 0.5 to 8% by weight (e.g., about 1 to 5% by weight). The acetic acid stream (3B) may have a water concentration of, for example, about 0 to 15% by weight (e.g., about 0.3 to 10% by weight) and preferably about 0.5 to 5% by weight (e.g., about 1 to 3% by weight). The acetic acid stream (3B) may have a dimethyl ether concentration of, for example, about 0 to 1% by weight (e.g., about 1 ppm to 0.8% by weight) and preferably about 5 ppm to 0.5% by weight (e.g., about 10 to 2000 ppm) or may have a dimethyl ether concentration substantially not more than detection limit. The acetic acid stream or side-cut stream (3B) contains these components, inevitable contaminants (including impurities or by-products), and acetic acid as the remainder. The acetic acid stream (3B) may have an acetic acid concentration of, for example, about 87 to 99% by weight (e.g., about 88 to 98% by weight) and preferably about 90 to 97% by weight (e.g., about 90 to 95% by weight).

The bottom liquid stream (higher boiling point stream or higher boiling point fraction) (3C) (the line 31) may have a concentration of each of PRC's (typically, acetaldehyde) of, for example, about 0 to 2000 ppm (e.g., about 0 to 1000 ppm), preferably about 0 to 500 ppm (e.g., about 1 to 100 ppm), and more preferably about 0 to 50 ppm or may have the PRC concentration substantially not more than detection limit. The bottom liquid stream (3C) may have a methyl iodide concentration of, for example, about 0 to 15% by weight (e.g., about 0.01 to 10% by weight), preferably about 0.1 to 8% by weight (e.g., about 0.2 to 5% by weight), and more preferably about 0.5 to 3% by weight. The bottom liquid stream (3C) may have each of a methyl acetate concentration and water concentration of, for example, about 0 to 15% by weight (e.g., about 0.1 to 10% by weight), preferably about 0.3 to 8% by weight (e.g., about 0.5 to 5% by weight), and more preferably about 0.7 to 3% by weight (e.g., about 1 to 2% by weight). The bottom liquid stream (3C) may have an acetic acid concentration of, for example, about 60 to 99% by weight (e.g., about 70 to 99% by weight), preferably about 80 to 98% by weight (e.g., about 85 to 98% by weight), and more preferably about 90 to 98% by weight. The bottom liquid stream (3C) may have a dimethyl ether concentration of, for example, about 0 to 1000 ppm (e.g., about 0 to 100 ppm) and preferably about 0 to 50 ppm (e.g., about 0 to 10 ppm) or may have a dimethyl ether concentration substantially not more than detection limit.

(5) Second Distillation Step (Distillation Column)

In the embodiment shown in FIG. 1, the first overhead stream (3A) [in the embodiment illustrated, the condensate from the liquid-liquid separation step (4)] is fed, via the feed line 43b and/or 44, to the second distillation step (distillation column) (5) and is distilled (e.g., azeotropically distilled) without supply (or addition) of water. With distilling the first overhead stream (3A), a portion of water in the first overhead stream (3A) is transferred or rises to an upper position than the feed port of the distillation column (5) to form a second mixture (for example, a biphasically separable second mixture by condensation) having an increased amount of water by transfer or distribution of water. The second mixture is withdrawn as a second overhead stream (5A), and the lower stream or bottom stream (5C), which has a decreased amount of water by transfer of water, is withdrawn from a lower position than the feed port. Specifically, the water in the first overhead stream (3A) is transferred to the second overhead stream (5A) as the upper stream predominantly than the lower stream or bottom stream (5C). Such a distributive distillation enables the second overhead stream (5A) to have a significantly higher PRC's (in particular, acetaldehyde) concentration than the first overhead stream or first mixture (3A) fed to the distillation column (5). The second overhead stream (5A) may be condensed and biphasically separated to form an aqueous phase having further effectively concentrated PRC's.

The second distillation step (distillation column) (5) forms the second mixture (5A) to which water is transferred or distributed predominantly than usual and the lower stream or bottom stream (5C) to which water is transferred or distributed less dominant than usual.

The second mixture having an increased water content is withdrawn as the upper stream. The second mixture is not limited to the overhead stream (5A). As shown by a dotted line in FIG. 1, the second mixture may be withdrawn as the side-cut stream (5B) via a line 63. Specifically, according to the height level (or position) of the second mixture formed in the distillation column, if the second mixture is withdrawn as the side-cut stream (5B), the first mixture (3A) has a concentration/amount of water lower than that in the lower stream or bottom stream (5C). Thus the second mixture can biphasically be separated to form an aqueous phase having effectively concentrated PRC's. The second mixture may be withdrawn as both overhead stream (5A) and side-cut stream (5B).

The second mixture may form a mixture containing water and having an azeotropic composition (for example, an azeotropic mixture biphasically separable by condensation). The formation of the azeotropic mixture increases the distribution amount (transfer amount) of water to the second mixture (5A)(5B) effectively and decreases the distribution amount (transfer amount) of water to the lower stream or bottom stream (5C) effectively, compared with the amount of water in the mixture in the original vapor-liquid equilibrium. Thus, by withdrawing the azeotropic mixture (second mixture) as the upper stream [overhead stream (5A) and/or the side-cut stream (5B)], condensing the withdrawn mixture to separate the condensate into two phases, an aqueous phase having effectively concentrated PRC's is obtainable.

The distillation of the first mixture (3A) may form a concentration zone of PRC's and methyl iodide at an upper position than the feed port of the second distillation step (distillation column) (5) and may allow at least a portion of water in the first mixture (3A) to move upward to the concentration zone; and a stream (second mixture) of the concentration zone may be withdrawn as the upper stream (5A)(5B) (i.e., the overhead stream (5A) and/or the side-cut stream (5B)). In this embodiment, by withdrawing the water rising in the distillation column (5) as the overhead stream (5A) and/or the side-cut stream (5B) from the distillation column (5), water can be separated (or removed) without falling in the distillation column (5). By liquid-liquid separating the withdrawn overhead stream (5A) and/or side-cut stream (5B), water (or an aqueous phase) is separable. Specifically, the falling of water within the distillation column (5) can be prevented (or suppressed) by simply withdrawing the overhead stream (5A) and/or the side-cut stream (5B), and removing the whole or most of the resulting aqueous phase from the system without refluxing the aqueous phase to the distillation column (5) (or while refluxing a portion of the aqueous phase). The first mixture (3A) may be distilled in a distillation column provided with a means that allows a vapor or evaporation fraction (a vapor or evaporation fraction in the first mixture) to rise to the concentration zone and that allows a liquid (a liquefied fraction) falling from the concentration zone to be prevented (or suppressed). The means may include, for example, a tray or receiver such as a chimney tray as described later. From the tray or receiver such as a chimney tray, the whole amount of the side-cut stream (5B) may be withdrawn.

Assuming that the total number of plates of the distillation column is 100 and the bottom is the "zeroth" (0th) plate, the position (feed port, or feed plate or tray) at which the first mixture or overhead stream (3A) [in the embodiment illustrated, the organic phase and/or the aqueous phase from the liquid-liquid separation step (4)] is fed to the second distillation column (5) may be about the 1st to the 50th plate (e.g., about the 3rd to the 45th plate), preferably the 4th to the 40th plate (e.g., about 5th to the 35th plate) from the bottom of the distillation column. For example, for a plate distillation column having a total actual number of plates of 43, the feed plate to which the first mixture (3A) is fed may be about the 1st to the 43th plate, preferably about the 2nd to the 40th plate, more preferably about the 4th to the 30th plate, about the 5th to the 20th plate, and about the 6th to the 10th plate from the bottom of the distillation column.

By the distillation in the second distillation step (5), the amount of water transferred or distributed from the first mixture or overhead stream (3A) to the upper stream (5A) and/or (5B) may be, for example, not less than 1% by weight (e.g., about 3 to 85% by weight), preferably not less than 5% by weight (e.g., about 5 to 80% by weight), more preferably not less than 10% by weight (e.g., about 15 to 75% by weight), and particularly not less than 30% by weight (e.g., about 30 to 70% by weight) or may be not less than 50% by weight (e.g., about 50 to 80% by weight). The amount of water to be transferred or distributed from the first mixture or overhead stream (3A) to the lower stream or bottom stream (5C) may be not more than 99% by weight (e.g., about 15 to 97% by weight), preferably not more than 95% by weight (e.g., about 20 to 95% by weight), more preferably not more than 90% by weight (e.g., about 25 to 85% by weight), and particularly not more than 70% by weight (e.g., about 30 to 70% by weight) or may be not more than 50% by weight (e.g., about 20 to 50% by weight). This predominant transfer or distribution of water to the upper stream (5A)(5B) forms the lower stream or bottom stream (5C) having a decreased amount of water (absolute amount)

compared with the amount of water in the first mixture (3A), and the upper stream (5A)(5B) having an increased amount of water (absolute amount) or an increased water concentration compared with the amount or concentration of water in the first mixture (3A). The second mixture (or azeotropic mixture) formed in the second distillation column (5) can be withdrawn as the upper stream (5A)(5B) to form two phases (an organic phase and an aqueous phase). For example, in a case where the azeotropic mixture having a concentration of water over a solubility of water in the organic phase is separated into two phases, the aqueous phase contains PRC's (in particular, acetaldehyde) selectively. Thus, simple removal of the aqueous phase, in which PRC's are successfully concentrated, from the system allows efficient removal of PRC's (in particular, acetaldehyde) without additional supply of water for water extraction.

When the concentration of water in the lower stream or bottom stream (5C) is decreased by distillation (or azeotropic distillation) of the first mixture (3A), the lower stream or bottom stream (5C) has a further decreased concentration of acetaldehyde, which has a high affinity with water. Accordingly, the acetaldehyde concentration in the lower stream or bottom stream (5C) can be reduced, and the separation efficiency of acetaldehyde from the upper stream (5A)(5B) is successfully improved. Such an advantage is not found in the conventional an.

By the distillation of the first mixture (3A), the lower stream or bottom stream (5C) may have a ratio ($H_2O$/MeI) of water ($H_2O$) relative to methyl iodide (MeI) lower than the first mixture (3A), or the second mixture or upper stream (5A)(5B) may have such a ratio ($H_2O$/MeI) higher than the first mixture (3A). The first mixture or first overhead stream (3A) may have a weight ratio $H_2O$/MeI of, for example, about 0.0001 to 10000, preferably about 0.001 to 1000, and more preferably about 0.005 to 500 or may have a weight ratio $H_2O$/MeI of about 0.01 to 100 (e.g., about 0.05 to 50). The lower stream or bottom stream (5C) may have a weight ratio $H_2O$/MeI of, for example, about 0.00005 to 5000, preferably about 0.0005 to 5000, and more preferably about 0.01 to 2500 or may have a weight ratio $H_2O$/MeI of about 0.005 to 500 (e.g., about 0.1 to 250). The second mixture or upper stream (5A)(5B) may have a weight ratio $H_2O$/MeI of about 0.0002 to 5000, preferably 0.002 to 500, and more preferably 0.01 to 250 or may have a weight ratio $H_2O$/MeI of about 0.05 to 50 (e.g., about 0.1 to 25).

The liquid-liquid separable second mixture (for example, an azeotropic mixture) can be formed by controlling the concentrations of components (concentration of each of acetaldehyde, methyl iodide, water, methyl acetate, acetic acid, or other components) in the first mixture or overhead stream (3A) and the distillation condition. Specifically, the distillation conditions (for example, an azeotropic condition) of acetaldehyde, methyl iodide, water, methyl acetate, acetic acid, and other slight amounts of impurities is achievable by regulating distillation conditions such as a concentration of each component, a reflux amount, and a theoretical number of plates. Too large a theoretical number of plates or too large a reflux amount makes the acetaldehyde concentration in the top of the column excessively high. This fails to form an azeotropic composition containing water in the top of the column, and the azeotropic composition is formed between the feed port (feed plate) and the column top plate. Thus the concentration of water around the top of distillation column is extremely low, and acetaldehyde is not concentrated to a concentration as high as that derived from calculation. In this respect, the distillation explained above is different from the ordinary distillation operation.

Meanwhile, the decrease in water concentration causes the decrease in acetaldehyde separation efficiency. Specifically, when the concentration of water is increased not at the top of the column but at a zone that is around the middle of the column and that has no discharging port (or port for withdrawing a stream to the outside of the system), acetaldehyde is concentrated to a high concentration at this zone; acetaldehyde is difficult to evaporate due to decrease in vapor pressure of acetaldehyde. Thus acetaldehyde is difficult to transfer (concentrate) from around the middle to the top of the column and is not efficiently concentrated in the top of the column (the concentration rate (or ratio) of acetaldehyde is hard to increase considering a large theoretical number of plates and a large reflux amount). Such a phenomenon is also found in the conventional art or the water extractive distillation described in the PTLs.

In contrast, due to a strong affinity of acetaldehyde (AD) with water, distributive distillation achieves easy concentration and separation of acetaldehyde (AD) under conditions that water is transferred upward from the feed port (feed plate) or to an upper position than the feed port (feed plate) and the lower stream or bottom stream has a water concentration lower than the first mixture (3A). This concentration or separation is achievable without utilizing the ordinary theoretical number of plates or reflux amount necessary for separating acetaldehyde (AD). Furthermore, after the distillation, since the upper stream (5A)(5B) which contains sufficient water is biphasically separated into a methyl iodide (MeI) phase and an aqueous phase, acetaldehyde (AD) dissolved in the aqueous phase can automatically be removed by removing the aqueous phase. Thus, the process conditions make the process simple without the conventional art in which acetaldehyde (AD) concentrated in the methyl iodide (MeI) phase is purposely withdrawn and is then additionally subjected to water extraction or in which water is fed to an acetaldehyde (AD)-concentrating column for water extractive distillation.

Incidentally, too high an acetaldehyde (AD) concentration fails to satisfy distributive distillation or azeotropic distillation conditions. The distributive distillation or azeotropic distillation conditions are sometimes unsatisfied according to the change in compositions of other components. Thus the distributive distillation or azeotropic distillation conditions should be optimized by regulating the theoretical number of plates, the reflux amount, the feed composition, or others. The theoretical number of plates can be regulated by withdrawing the distillate (or overhead) from the top of the column as well as by disposing a side-cut plate below the top of the column. The reflux amount can be regulated by varying a load of a reboiler in the bottom of the column. The composition of the feed liquid [the first overhead stream or first mixture (3A)] can be regulated according to a mixing ratio of the organic phase and the aqueous phase in the decanter 4. A higher feed ratio of the aqueous phase increases an amount of rising water (distribution amount or azeotrope amount) in the distillation column and thus increases the amount of the aqueous phase from the upper stream (5A)(5B) to remove acetaldehyde in a larger quantity.

In a case where the second mixture is withdrawn as the overhead stream (5A) in the distributive distillation or azeotropic distillation, water may be fed from a feed port (feed plate) below the top of the distillation column for distribution or azeotrope. In a case where the second mixture is withdrawn as the side-cut stream (5B), water may be fed from a feed port (feed plate) below a withdrawing port (side-cut plate) for distribution or azeotrope.

The internal temperature of the distillation column of the second distillation step (5) depends on an internal pressure thereof. At the internal pressure of an atmospheric pressure, the distillation column may have a column top temperature of, for example, about 15 to 120° C. (e.g., about 18 to 100° C.), preferably about 20 to 90° C. (e.g., about 20 to 80° C.), and more preferably about 20 to 70° C. (e.g., about 25 to 70° C.), or may have a column bottom temperature of, for example, about 35 to 150° C. (preferably about 40 to 120° C.). The distillation column may have a column top pressure (absolute pressure) of, for example, about 0.1 to 0.5 MPa. In the second distillation step (5), other distillation conditions (e.g., the theoretical number of plates of the distillation column, and the reflux ratio) may be the same as those in the first distillation step (3).

The second mixture (for example, an azeotropic mixture) may have a composition corresponding to the composition of the second overhead stream (5A) (a mixture of an aqueous phase and an organic phase when the second mixture is separated into these phases; a mixture in a line 53, a mixture of a stream in a line 61 and a stream in a line 62) in the process shown in FIG. 1.

The second mixture or concentration zone (the zone in which aldehydes are concentrated) (a fluid or stream in a concentration zone formed in a zone between the feeding port of the distillation column (5) and the withdrawing port for the overhead of the distillation column (5)) may have a PRC (e.g., acetaldehyde) concentration at which the PRC can form an azeotrope with water, for example, not more than 90% by weight (e.g., not more than 80% by weight), preferably not more than 70% by weight (e.g., not more than 60% by weight), and more preferably not more than 50% by weight (e.g., not more than 40% by weight) or may have a PRC concentration of not more than 30% by weight, preferably not more than 28% by weight, and more preferably not more than 25% by weight (e.g., not more than 24% by weight).

Each of the second overhead stream (5A) (a mixture of an aqueous phase and an organic phase when the stream is separated into these phases; a mixture in a line 53, a mixture of a stream in a line 61 and a stream a line 62) and the side-cut stream (5B) (a mixture of an aqueous phase and an organic phase when the stream is separated into these phases; a mixture in a line 63) may have a concentration of each of PRC's (e.g., acetaldehyde) of, for example, about 0.5 to 40% by weight (e.g., about 1 to 20% by weight), preferably about 2 to 10% by weight (e.g., about 3 to 7% by weight); or may have the PRC concentration of about 0.1 to 10% by weight, preferably about 0.5 to 7% by weight, and more preferably about 1 to 5% by weight. Each of the second overhead stream (5A) and the side-cut stream (5B) may have a methyl iodide concentration of, for example, about 1 to 99% by weight (e.g., about 5 to 97% by weight), preferably about 10 to 95% by weight (e.g., about 20 to 95% by weight), and more preferably about 30 to 95% by weight; or may have a methyl iodide concentration of about 50 to 99% by weight (e.g., about 65 to 98% by weight), preferably about 75 to 98% by weight (e.g., about 85 to 97% by weight), and more preferably about 90 to 97% by weight. Each of the second overhead stream (5A) and the side-cut stream (5B) may have a methyl acetate concentration of, for example, about 0.1 to 20% by weight (e.g., about 0.5 to 10% by weight) and preferably about 0.7 to 7% by weight (e.g., about 0.7 to 5% by weight) or may have a methyl acetate concentration of about 0.5 to 5% by weight (e.g., about 0.5 to 3% by weight). Each of the second overhead stream (5A) and the side-cut stream (5B) may have an acetic acid concentration of, for example, about 0 to 5% by weight (e.g., about 0.01 to 3% by weight) and preferably about 0.1 to 2% by weight or may have an acetic acid concentration substantially not more than detection limit. Each of the second overhead stream (5A) and the side-cut stream (5B) may have a water concentration of, for example, about 0.1 to 20% by weight (e.g., about 0.3 to 10% by weight), preferably about 0.5 to 5% by weight, and more preferably about 0.8 to 3% by weight (e.g., about 1 to 2% by weight). Each of the second overhead stream (5A) and the side-cut stream (5B) may have a dimethyl ether concentration of, for example, about 0 to 3% by weight (e.g., about 0.0001 to 2% by weight) and preferably about 0.001 to 1.7% by weight (e.g., about 0.01 to 1.5% by weight) or may a dimethyl ether concentration of about 0.1 to 1% by weight.

In a case where the second overhead stream (5A) and/or the side-cut stream (5B), for example, at least the second overhead stream (5A), is liquid-liquid separated (or forms an organic phase and an aqueous phase), the organic phase (lines 64, 68) may have a concentration of each of PRC's of, for example, about 0.1 to 20% by weight (e.g., about 0.5 to 20% by weight) and preferably about 1 to 10% by weight (e.g., about 2 to 5% by weight). The organic phase may have a methyl iodide concentration of, for example, about 50 to 99% by weight (e.g., about 60 to 98% by weight) and preferably about 70 to 97% by weight (e.g., about 80 to 95% by weight), or may have a methyl iodide concentration of about 85 to 98% by weight (e.g., about 90 to 97% by weight). The organic phase may have a methyl acetate concentration of, for example, about 0.1 to 20% by weight (e.g., about 0.5 to 10% by weight) and preferably about 0.7 to 7% by weight (e.g., about 1 to 5% by weight), or may have a methyl acetate concentration of about 2 to 4% by weight; or may have a methyl acetate concentration of about 0.3 to 7% by weight (e.g., about 0.5 to 5% by weight). The organic phase may have an acetic acid concentration of, for example, about 0 to 5% by weight (e.g., about 0.001 to 3% by weight), preferably about 0.01 to 2% by weight, and about 0.1 to 0.5% by weight, or may have an acetic acid concentration substantially not more than detection limit. The organic phase may have a water concentration of about 0 to 5% by weight (e.g., about 0.01 to 3% by weight) and preferably about 0.05 to 1% by weight (e.g., about 0.1 to 0.3% by weight). The organic phase may have a dimethyl ether concentration of, for example, about 0 to 3% by weight (e.g., about 1 ppm to 2% by weight) and preferably about 10 ppm to 1.5% by weight (e.g., about 100 to 5000 ppm).

In a case where the second overhead stream (5A) and/or the side-cut stream (5B), for example, at least the second overhead stream (5A), is liquid-liquid separated (or forms an organic phase and an aqueous phase), the aqueous phase (lines 66, 69) may have a concentration of each of PRC's of about 1 to 50% by weight (e.g., about 5 to 40% by weight) and preferably about 10 to 30% by weight (e.g., about 15 to 25% by weight). The aqueous phase may have a methyl iodide concentration of, for example, about 0.01 to 10% by weight (e.g., about 0.1 to 5% by weight) and preferably about 0.5 to 4% by weight (e.g., about 0.8 to 3% by weight), or may have a methyl iodide concentration of about 1 to 2% by weight. The aqueous phase may have a methyl acetate concentration of, for example, about 0.1 to 10% by weight (e.g., about 0.2 to 5% by weight) and preferably about 0.3 to 2% by weight (e.g., about 0.5 to 1% by weight), or may have a methyl acetate concentration of about 0.1 to 1.5% by weight. The aqueous phase may have an acetic acid concentration of, for example, about 0 to 5% by weight (e.g., about 0.001 to 3% by weight) and preferably about 0.01 to 2% by weight, or may have an acetic acid concentration substantially not more than detection limit (0% by weight). The aqueous phase may have a dimethyl ether concentration of, for example, about 0 to 3% by weight (e.g., about 1 ppm to 2% by weight) and preferably about 0.001 to 1.5% by weight (e.g., about 0.01 to 1% by weight). The aqueous phase usually contains these components, inevitable contaminants (including impurities or byproduct), and water as the remainder. The aqueous phase may have a water concentration of, for example, about 50 to 95% by weight (e.g., about 60 to 93% by weight) and preferably about 70 to 90% by weight (e.g., about 75 to 85% by weight).

The aqueous phase (lines 66, 69), which is a phase liquid-liquid separated from the second overhead stream (5A) and/or the side-cut stream (5B) [for example, at least the second overhead stream (5A)], contains enriched PRC's (e.g., acetaldehyde) and has a PRC's (e.g., acetaldehyde) concentration higher than a methyl iodide concentration. The aqueous phase may have a ratio (AD/MeI) of acetaldehyde (AD) relative to methyl iodide (MeI) of, for example, about 3/1 to 50/1 (e.g., about 4/1 to 40/1) and preferably about 5/1 to 30/1 (e.g., about 7/1 to 20/1), or may be about 8/1 to 15/1 (e.g., about 10/1 to 15/1).

The second overhead stream (5A) (the line 53 just before a condenser C3) (a mixture of an aqueous phase and an organic phase when the second overhead stream is separated into these phases) may have a temperature at an atmospheric pressure of, for example, about 15 to 110° C. (e.g., about 18 to 90° C.) and preferably about 20 to 80° C. (e.g., about 20 to 70° C.).

The side-cut stream (5B) (the line 63) may have a temperature at an atmospheric pressure of, for example, about 15 to 110° C. (e.g., about 20 to 90° C.) and preferably about 25 to 80° C. (e.g., about 30 to 70° C.).

In a case where the first overhead stream (3A) to be fed to the distillation column 5 is a homogeneous liquid or a mixture of an aqueous phase and an organic phase, the lower stream or bottom stream (5C) (a line 52) may have an acetaldehyde concentration of, for example, about 0 to 1% by weight (e.g., about 1 to 5000 ppm), preferably about 0 to 2500 ppm (e.g., about 5 to 1000 ppm), about 10 to 100 ppm, and about 20 to 50 ppm, or may have an acetaldehyde concentration substantially not more than detection limit. The lower stream or bottom stream (5C) may have a methyl iodide concentration of, for example, about 5 to 99% by weight (e.g., about 10 to 95% by weight), preferably about 20 to 90% by weight (e.g., about 30 to 85% by weight), and more preferably about 40 to 85% by weight (e.g., about 50 to 80% by weight). The lower stream or bottom stream (5C) may have a methyl acetate concentration of, for example, about 0 to 30% by weight (e.g., about 0.1 to 25% by weight) and preferably about 1 to 20% by weight (e.g., about 5 to 20% by weight), or may have a methyl acetate concentration of about 7 to 17% by weight (e.g., about 10 to 15% by weight). The lower stream or bottom stream (5C) may have an acetic acid concentration of, for example, about 0 to 12% by weight (e.g., about 0.1 to 10% by weight) and preferably about 0.5 to 8% by weight (e.g., about 1 to 7% by weight); or may have an acetic acid concentration of about 1 to 5% by weight (e.g., about 1 to 3% by weight). The lower stream or bottom stream (5C) may have a water concentration of, for example, about 0 to 80% by weight (e.g., about 0.001 to 70% by weight), preferably about 0.005 to 60% by weight (e.g., about 0.01 to 50% by weight), and more preferably about 0.05 to 40% by weight (e.g., about 0.1 to 30% by weight); or may have a water concentration of about 0.2 to 30% by weight (e.g., about 0.25 to 20% by weight) and preferably about 0.3 to 10% by weight (e.g., about 0.35 to 5% by weight). The lower stream or bottom stream (5C) may have a dimethyl ether concentration of, for example, about 0 to 2000 ppm (e.g., about 0.001 to 1500 ppm), preferably about 0.01 to 500 ppm (e.g., about 0.1 to 100 ppm), and more preferably about 0.2 to 10 ppm.

In a case where the first overhead stream (3A) to be fed to the distillation column 5 is an organic phase formed in liquid-liquid separation, the lower stream or bottom stream (5C) may have an acetaldehyde concentration of, for example, about 0 to 1% by weight (e.g., about 1 to 5000 ppm), preferably about 0 to 2500 ppm (e.g., about 5 to 1000 ppm), and more preferably about 10 to 100 ppm (e.g., about 20 to 50 ppm), or may have an acetaldehyde concentration substantially not more than detection limit. The lower stream or bottom stream (5C) may have a methyl iodide concentration of, for example, about 10 to 99% by weight (e.g., about 30 to 95% by weight), preferably about 40 to 90% by weight (e.g., about 50 to 85% by weight), and more preferably about 60 to 85% by weight. The lower stream or bottom stream (5C) may have a methyl acetate concentration of, for example, about 0 to 30% by weight (e.g., about 0.1 to 25% by weight) and preferably about 1 to 20% by weight (e.g., about 5 to 20% by weight), or may have a methyl acetate concentration of about 7 to 17% by weight (e.g., about 10 to 15% by weight). The lower stream or bottom stream (5C) may have an acetic acid concentration of, for example, about 0 to 12% by weight (e.g., about 0.1 to 10% by weight) and preferably about 0.5 to 8% by weight (e.g., about 1 to 7% by weight); or may have an acetic acid concentration of about 1 to 5% by weight (e.g., about 1 to 3% by weight). The lower stream or bottom stream (5C) may have a water concentration of about 0 to 52% by weight (e.g., about 0.01 to 42% by weight), preferably about 0.1 to 32% by weight (e.g., about 0.2 to 22% by weight), and more preferably about 0.5 to 11% by weight (e.g., about 1 to 6% by weight); or may have a water concentration of about 0 to 6% by weight (e.g., about 0.1 to 4% by weight) and preferably about 0.3 to 3% by weight (e.g., about 0.5 to 2% by weight). The lower stream or bottom stream (5C) may have a dimethyl ether concentration of, for example, about 0 to 2000 ppm (e.g., about 0.001 to 1500 ppm), preferably about 0.01 to 500 ppm (e.g., about 0.1 to 100 ppm), and more preferably about 0.2 to 10 ppm.

In a case where the first overhead stream (3A) to be fed to the distillation column 5 is an aqueous phase formed in liquid-liquid separation, the lower stream or bottom stream (5C) may have an acetaldehyde concentration of, for example, about 0 to 1% by weight (e.g., about 1 to 5000 ppm) and preferably about 0 to 2500 ppm (e.g., about 10 to 1000 ppm), or may have an acetaldehyde concentration substantially not more than detection limit. The lower stream or bottom stream (5C) may have a methyl iodide concentration of, for example, about 0.1 to 30% by weight (e.g., about 1 to 25% by weight) and preferably about 3 to 20% by weight (e.g., about 5 to 15% by weight); or may have a methyl iodide concentration of not less than 1.5% by weight (e.g., about 2 to 50% by weight), preferably not less than 2% by weight (e.g., about 3 to 40% by weight), and more preferably not less than 4% by weight (e.g., about 5 to 30% by weight). The lower stream or bottom stream (5C) may have a methyl acetate concentration of, for example, about 1 to 30% by weight (e.g., about 3 to 25% by weight) and preferably about 5 to 20% by weight (e.g., about 7 to 15% by weight). The lower stream or bottom stream (5C) may have an acetic acid concentration of, for example, about 5 to 60% by weight (e.g., about 10 to 50% by weight) and preferably about 20 to 40% by weight (e.g., about 25 to 35% by weight). The lower stream or bottom stream (5C) may have a water concentration of, for example, about 10 to 92% by weight (e.g., about 25 to 82% by weight) and preferably about 30 to 77% by weight (e.g., about 40 to 72% by weight). The lower stream or bottom stream (5C) may have a dimethyl ether concentration of, for example, about 0 to 2000 ppm (e.g., about 1 to 1500 ppm) and preferably about 10 to 1000 ppm (e.g., about 50 to 500 ppm).

The lower stream or bottom stream (5C) may have a temperature at an atmospheric pressure of, for example, about 30 to 160° C. (e.g., about 35 to 120° C.) and preferably about 40 to 100° C. (e.g., about 40 to 80° C.).

The lower stream or bottom stream (5C) has a concentration of each of PRC's (e.g., acetaldehyde) significantly lower than the first overhead stream (3A). The lower stream or bottom stream (5C) may have a concentration of each of PRC's of, for example, about 1 to 800 ppm and preferably about 10 to 300 ppm, or may have the PRC concentration substantially not more than detection limit (0% by weight). Thus the lower stream or bottom stream (5C) may be recycled to the reaction system vie the line 52. If necessary, via the line 52 the lower stream or bottom stream (5C) may be subjected to additional distillation and then optional water extraction to remove and separate PRC's (e.g., acetaldehyde).

According to one embodiment of the present invention, the first overhead stream (3A) is distilled in the second distillation step (5) to form the second overhead stream (5A) and/or the side-cut stream (5B), and the bottom stream (5C). The distillation column of the second distillation step (5) may function as an aldehyde-removing column. Thus the first overhead stream (3A) contains at least one PRC (e.g., acetaldehyde), methyl iodide, and water and has a composition corresponding to the composition of the first mixture. The first overhead stream or first mixture (3A) may further contain methyl acetate. As described above, the first overhead stream or first mixture (3A) may further contain at least one selected from acetic acid, methanol, dimethyl ether, and an acetaldehyde derivative (e.g., an aldehyde, a ketone, an alkyl iodide, a higher boiling point alkanecarboxylic acid, and an alkane), a dialkyl ether, or other compounds.

The distillation column of the distillation step (5) is provided with at least one receiver (e.g., chimney tray). The distillation column may be provided with a plurality of receivers (chimney trays). For a distillation column having a plurality of receivers (chimney trays), the extractant may be added to a concentration zone that is formed above the uppermost chimney tray via a line 50.

(6) Liquid-Liquid Separation Step

In the embodiment shown in FIG. 1, the second overhead stream (5A) is cooled and condensed in the condenser C3 on the withdrawing line 53 and is then biphasically separated in a separation unit (decanter) 6a to form an organic phase (a lower phase) and an aqueous phase (an upper phase). The organic phase is refluxed or recycled to the distillation column (for example, the top of the column) of the second distillation step (5) via the reflux line 61. A first portion of the aqueous phase from the decanter 6a passes through the line 62 and is cooled in a cooling unit (a cooler) C4 on a line 66 to form two phases (an organic phase and an aqueous phase) in the decanter 6c. A second portion of the aqueous phase from the decanter 6a is recycled to the distillation column of the second distillation step (5) via a line 67. The organic phase (a heavy phase rich in methyl iodide or a lower phase) from the decanter 6c is recycled to the distillation column of the second distillation step (5) via a line 68.

The aqueous phase from the decanter 6c is fed to the third distillation step (distillation column) (7) via a line 69 for further separating PRC's and methyl iodide from each other.

Each of the condensate (the aqueous phase, the organic phase, or a mixture thereof) cooled in the condenser C3 and the liquid stream (and the aqueous phase and the organic phase) cooled in the cooling unit C4 may have a temperature of, for example, about 0 to 60° C. (e.g., about 1 to 50° C.), preferably about 3 to 30° C. (e.g., about 3 to 20° C.), and more preferably about 5 to 15° C.

(Miscible Solvent)

In order to efficiently separate methyl iodide and PRC's (e.g., acetaldehyde) from each other in the presence of methyl acetate, a miscible solvent that is miscible with an organic phase may be fed to a stream (an organic phase and/or an aqueous phase) which is recycled to the second distillation step (5). The miscible solvent may include a solvent having a high affinity with either an amphipathic compound (such as methyl acetate) or PRC's; a solvent capable of inhibiting formation of an azeotropic composition of an amphipathic compound (such as methyl acetate) and other compounds (in particular, water, PRC's such as acetaldehyde); and a solvent that lowers a volatility (vapor pressure) of an amphipathic compound (such as methyl acetate); or other solvents. The miscible solvent usually changes an azeotropic composition (or gas composition) of PRC's and methyl iodide in the presence of methyl acetate, or prevents formation of an azeotropic composition and causes a concentration distribution of methyl acetate in the height direction of the distillation column; and/or lowers the volatility (vapor pressure) of methyl acetate. Thus addition of the miscible solvent enables the concentration of methyl acetate in the aqueous phase to be reduced, and enables mixing of methyl iodide in the aqueous phase to be prevented.

The miscible solvent may be a miscible solvent present in the system [for example, a solvent present in the acetic acid production process or a solvent produced in the process, or a process stream (e.g., an aqueous solvent such as an aqueous phase or an aqueous extract 67)] or may be a miscible solvent from the outside of the system (for example, at least one selected from water, acetic acid, and other compounds). The miscible solvent may have a boiling point higher than methyl iodide and PRC's (e.g., acetaldehyde). The process stream may be a process stream capable of lowering the volatility (vapor pressure) of methyl acetate (e.g., a crude acetic acid stream, an overhead stream, a bottom stream, and a recycle stream). The miscible solvent may be an amphipathic solvent. The miscible solvent usually contains at least one member selected from water, acetic acid, methyl iodide, and methanol. The miscible solvent which is fed from outside may be water or other solvents, and is usually an organic miscible solvent, for example, a miscible solvent containing acetic acid (such as acetic acid or crude acetic acid) in practical embodiments. A preferred miscible solvent may be an aqueous phase separated from the upper stream (5A)(5B) [for example, an aqueous phase produced in the second liquid-liquid separation step (6)] or may be a process stream containing acetic acid (e.g., a crude acetic acid stream).

In the embodiment shown in FIG. 1, to the distillation column of the second distillation step (5) is fed the miscible solvent via a feed line 70 and/or the aqueous phase (or extract) via the line 67, and distillation in the presence of the miscible solvent separates methyl iodide and PRC's (e.g., acetaldehyde) in the presence (coexistence) of an amphipathic compound (such as methyl acetate).

The miscible solvent may directly be fed to the distillation column of the second distillation step (5) via the feed line 70 or may indirectly fed to the distillation column of the second distillation step (5) via a recycle line 65 or other lines. The miscible solvent is usually fed to an intermediate or lower position of the distillation column in height in order to prevent methyl acetate concentrating in a space between the lower feed port and the feed plate of the first overhead stream (3A) in practical embodiments. The miscible solvent may be fed to an upper position than the intermediate of the distillation column in height. Incidentally, concentrating methyl acetate in the space can be prevented by avoiding (or inhibiting) the azeotropic composition, by lowering the volatility (vapor pressure) of methyl acetate, or by other means, as described above.

The miscible solvent may have the same temperature as the extractant has. The miscible solvent may be added to the distillation column as a heated solvent having the same temperature as the temperature of the extractant or as a vaporized form (or steam).

The amount to be added of the miscible solvent may be not more than 30% by weight, for example, about 0.01 to 20% by weight (e.g., about 0.1 to 15% by weight), and preferably about 0.5 to 10% by weight (e.g., about 1 to 5% by weight) relative to the amount of the liquid falling from the concentration zone (the amount of the liquid falling in the tray(s)) in the distillation step (5).

In a case where the miscible solvent (e.g., acetic acid) is distilled in the distillation column of the second distillation step (5) together with an organic phase from the liquid-liquid separation step (6) or other steps [for example, distillation of the organic phase formed in the hold tank 6b and the miscible solvent (e.g., acetic acid) from the line 70, or distillation of the organic phase and the miscible solvent (e.g., acetic acid) fed from a distillation plate lower than a position withdrawing the side-cut stream (5B)], a plurality of components such as methyl iodide, acetaldehyde, water, or other compounds may combinationally form an azeotrope (or an azeotropic composition) in the second distillation column (5) (or does not form an azeotrope with methyl acetate) or may simply lower (or reduce) the vapor pressure of methyl acetate. Even in such a case, the concentration of methyl acetate in the process liquid (a condensate, an upper phase and/or a lower phase, in particular, an upper phase containing acetaldehyde) fed to the third distillation step (7) via the line 69 may be decreased to reduce the concentration of methyl iodide dissolved in the aqueous phase.

In the production process of acetic acid, although it is preferred to use water in the system as a balanced water without supply of water from the outside of the system, recycling of the aqueous phase (for example, the aqueous phase via the line 67) to the distillation column (5) slightly increases the water concentration in the bottom stream (5C) (the line 52) of the distillation column (5), thereby changing the water balance in the system. In contrast, use of the organic miscible solvent such as acetic acid reduces the concentration of methyl acetate in the distillation column while maintaining the water balance in the system, thus reducing the amount of methyl iodide to be discharged. For example, the aqueous phase (for example, the aqueous phase in the system, such as in the line 67) is recycled to the distillation column (5) while the miscible solvent (e.g., acetic acid) is added to the distillation column (5), and the bottom stream (5C) (the line 52) from the distillation column (5) is recycled to the reaction system; this allows the concentration of methyl acetate in the distillation column to be reduced to the limit while preventing accumulation of water in the reaction system and also reduces the amount of methyl iodide to be discharged to the outside of the system.

The addition of the miscible solvent (e.g., acetic acid) may induce an aldol condensation in the distillation column of the second distillation step (5) to produce higher boiling point substances from acetaldehyde, which is to be concentrated in the top of the column, and thus can decrease separation of acetaldehyde. However, in a system having a high concentration of methyl iodide and a low concentration of water concentration, acetic acid only exhibits an extremely weak acidity. In such a system, the aldol condensation under an acidic condition is minimized and hardly affects the concentration of acetaldehyde.

Thus, by introducing the aqueous solvent (for example, the aqueous phase separated or aqueous extract 67) produced in the process and/or the miscible solvent into the distillation column of the second distillation step (5), two or three components selected from methyl iodide, water, and acetaldehyde form an azeotropic composition, methyl acetate to prevent the formation of an azeotrope or to simply lower the vapor pressure of methyl acetate. This results in significant decrease in concentration of methyl acetate in the aqueous phase.

Incidentally, in a case where an amount of acetic acid as the miscible solvent is too large, there is a possibility to increase a concentration of acetic acid in the upper stream (5A)(5B) and the aqueous phase or extract 67 and to increase a concentration of methyl iodide in the aqueous phase. However, such a situation is avoidable by feeding an appropriate amount of acetic acid.

(7) Distillation Step

The aqueous phase (a light phase rich in acetaldehyde or an upper phase) from the liquid-liquid separation step (6) is separated into a third overhead stream (lower boiling point stream) (7A) rich in a permanganate reducing compound (in particular, acetaldehyde) and methyl iodide, and a liquid stream rich in an extractant (higher boiling point stream, lower stream or bottom stream) (7B) in the third distillation step (distillation column) (7). The third overhead stream (lower boiling point stream) (7A) is cooled and condensed in a condenser C5; a first portion of the condensate is returned to the distillation column (7) of the third distillation step via a reflux line 73 for reflux, and a second portion of the condensate is fed to a fourth distillation step (8) via a feed line 74.

The internal temperature of the distillation column of the third distillation step (7) depends on an internal pressure thereof. At the internal pressure of an atmospheric pressure, the distillation column may have a column top temperature of, for example, about 10 to 90° C. (e.g., about 15 to 80° C.) and preferably about 20 to 70° C. (e.g., about 20 to 60° C.), or may have a column bottom temperature of, for example, about 70 to 170° C. (e.g., about 80 to 160° C.) and preferably about 90 to 150° C. (e.g., about 95 to 140 CC). The distillation column may have a column top pressure of, for example, about 0.1 to 0.5 MPa, preferably about 0.2 to 0.4 MPa and more preferably about 0.25 to 0.35 MPa in terms of absolute pressure.

The distillation column may have a theoretical number of plates of, for example, about 1 to 50 (e.g., about 2 to 40) and preferably about 3 to 30 (e.g., about 5 to 10). The reflux ratio of the distillation column may be, for example, about 1 to 1000 (e.g., about 2 to 500), preferably about 3 to 100 (e.g., about 4 to 50), and more preferably about 5 to 30.

The overhead stream (7A) or a condensate thereof (lines 72, 73, 74) is rich in acetaldehyde and has a lower methyl iodide concentration. The overhead stream (7A) or the condensate thereof also contains methyl acetate. The condensate of the overhead stream (7A) may have an acetaldehyde concentration of, for example, about 50 to 99.9% by weight (e.g., about 60 to 99% by weight), preferably about 70 to 98% by weight (e.g., about 75 to 97% by weight), and more preferably about 80 to 95% by weight (e.g., about 85 to 95% by weight). The condensate may have a methyl iodide concentration of, for example, about 0.1 to 20% by weight and preferably about 0.5 to 10% by weight (e.g., about 1 to 7% by weight) or may have a methyl iodide concentration of about 2 to 10% by weight (e.g., about 3 to 10% by weight). The condensate may have a methyl acetate concentration of, for example, about 0.1 to 20% by weight, preferably about 0.5 to 15% by weight (e.g., about 0.7 to 12% by weight), and more preferably about 1 to 10% by weight (e.g., about 1 to 5% by weight). The condensate of the overhead stream (7A) may have an acetic acid concentration of, for example, about 0 to 5% by weight, preferably about 0 to 3% by weight, and more preferably about 0 to 1% by weight. In some embodiments, the condensate of the overhead stream (7A) substantially contains no acetic acid (or has an acetic acid concentration not more than detection limit). The condensate of the overhead stream (7A) may have a water concentration of, for example, about 0 to 5% by weight (e.g., about 0 to 3% by weight), preferably 0 to 1% by weight (e.g., 0 to 0.1% by weight), or may have a water concentration not more than detection limit. The condensate may have a dimethyl ether concentration of, for example, about 1 ppm to 5% by weight (e.g., about 0.001 to 3% by weight), preferably about 0.01 to 2.5% by weight (e.g., about 0.1 to 2% by weight), and more preferably about 0.5 to 1.5% by weight.

The overhead stream (7A) may have a temperature at an atmospheric pressure of, for example, about 15 to 110° C. (e.g., about 20 to 90° C.) and preferably about 25 to 80° C. (e.g., about 30 to 70° C.), or may have a temperature at an atmospheric pressure of about 20 to 55° C. The condensate (lines 73, 74) of the overhead stream (7A) cooled in the condenser C5 may have a temperature of, for example, about 0 to 60° C. (e.g., about 5 to 45° C.) and preferably about 7 to 30° C. (e.g., about 10 to 30° C.).

The bottom liquid stream (7B) (a line 71) usually contains an extractant as a main component. The bottom liquid stream (7B) may contain, in addition to the extractant, small amounts of components such as acetaldehyde, methyl iodide, acetic acid, methyl acetate, methanol, dimethyl ether (DME), and impurities present in the system. The liquid stream (7B) may have an acetaldehyde concentration (on the basis of weight) of, for example, not more than 0.1% by weight (e.g., about 1 ppb to 0.1% by weight), preferably not more than 500 ppm (e.g., about 10 ppb to 300 ppm), and more preferably not more than 100 ppm (e.g., about 0.1 ppm to 100 ppm), or may have an acetaldehyde concentration substantially not more than detection limit (0% by weight). The liquid stream (7B) may have a methyl iodide concentration of, for example, not more than 1% by weight (e.g., about 1 ppm to 0.8% by weight) and preferably not more than 0.5% by weight (e.g., about 10 ppm to 0.1% by weight), or may have a methyl iodide concentration substantially not more than detection limit (0% by weight). The liquid stream (7B) may have a methyl acetate concentration of about 1 ppm to 4% by weight (e.g., about 5 ppm to 2% by weight) and preferably about 0.001 to 1% by weight (e.g., about 0.005 to 0.7% by weight). The liquid stream (7B) may have an acetic acid concentration of, for example, not more than 10% by weight (e.g., about 1 ppm to 10% by weight) and preferably not more than 7% by weight (e.g., about 0.001 to 5% by weight), or may have an acetic acid concentration substantially not more than detection limit (0% by weight). The liquid stream (7B) may have a dimethyl ether concentration of, for example, about 0 to 1000 ppm (e.g., about 0 to 100 ppm) and preferably about 0 to 50 ppm (e.g., about 0 to 10 ppm), or may have a dimethyl ether concentration substantially not more than detection limit (0% by weight). The bottom liquid stream (7B) usually contains these components, inevitable contaminants (including impurities or by-products), and water as the remainder. The bottom liquid stream (7B) may have a water concentration of, for example, about 90 to 99.99% by weight (e.g., about 93 to 99.98% by weight) and preferably about 95 to 99.95% by weight (e.g., about 97 to 99.9% by weight). The bottom liquid stream (7B) may be recycled, as an extractant in the distillation step (5), to the distillation step (5) via the bottom line 71.

The bottom liquid stream (7B) may have a temperature at an atmospheric pressure of, for example, about 70 to 160° C. (e.g., about 80 to 120° C.) and preferably about 85 to 110° C. (e.g., about 90 to 110° C.), or may have a temperature at an atmospheric pressure of about 95 to 105° C.

Probably because acetic acid and methyl acetate are predominantly transferred to the bottom liquid stream (7B), the third overhead stream (7A) seems to have each of a ratio (MeI/AC ratio) of methyl iodide (MeI) relative to acetic acid (AC) and a ratio (MeI/MA ratio) of methyl iodide (MeI) relative to methyl acetate (MA) higher than the liquid fed from the line 69.

The liquid stream (7B) may be removed or discharged to the outside of the system.

(8) Distillation Step

As described above, the overhead stream (7A) still contains methyl iodide, although the concentration of methyl iodide is low. Thus, the overhead stream (7A) may further be distilled in the distillation step (8) to reduce the concentration of methyl iodide. Specifically, the overhead stream (7A) from the distillation step (7) may further be distilled in the distillation step (8) to separate the overhead stream (7A) into an overhead stream (8A) and a bottom liquid stream (8B). Since the overhead stream (7A) has a concentrated (enriched) acetaldehyde, the distillation step (8) is preferably a water extractive distillation. In more details, water is added to the top of the distillation column (separation column) of the distillation step (8) via a feed line 82 for the water extractive distillation, and the overhead stream (8A) is directly or indirectly recycled to the reaction step (1) and the bottom liquid stream (8B) containing acetaldehyde is withdrawn via a line 81. In the embodiment shown in FIG. 1, the overhead stream (8A) is cooled and condensed in a condenser C6 on a line 83, a first portion of the condensate is returned to the distillation column (separation column) (8) via a reflux line 84 for reflux, and a second portion of the condensate is withdrawn via a line 85 and is recycled to the reaction step (1).

For such a water extractive distillation, the overhead stream (8A) or a condensate thereof, which has a ratio of methyl iodide relative to acetaldehyde larger than the liquid stream (8B), may produce a condensate having a high methyl iodide concentration. The concentrate may be recycled to the reaction step (reactor) (1) via a line 85.

For the water extractive distillation, the water may have the same temperature as the extractant. The water may be added as a warmed or heated water having the same temperature as the extractant or as a vaporized water (or steam).

The bottom liquid stream or aqueous bottom stream (8B) is rich in the extractant (in particular, water) and acetaldehyde. Thus the bottom liquid stream (8B) may be discharged to the outside of the system; or may further be distilled to separate a PRC's fraction and a water fraction from each other, the PRC's fraction may be discharged to the outside of the system, and the water fraction may be recycled as an extractant for the distillation step (5); or may be recycled to the reaction step (reactor) (1).

The internal temperature of the distillation column of the fourth distillation step (8) depends on an internal pressure thereof. At the internal pressure of an atmospheric pressure, the distillation column may have a column top temperature of, for example, about 10 to 90° C. (e.g., about 15 to 80° C.) and preferably about 20 to 70° C. (e.g., about 20 to 65° C.), or may have a column bottom temperature of, for example, about 15 to 110° C. (e.g., about 20 to 100° C.) and preferably about 25 to 80° C. (e.g., about 30 to 70° C.). The distillation column may have a column top pressure of, for example, about 0.1 to 0.5 MPa, preferably about 0.2 to 0.4 MPa, and more preferably about 0.25 to 0.35 MPa in terms of absolute pressure.

The distillation column may have a theoretical number of plates of, for example, about 1 to 50 (e.g., about 2 to 40) and preferably about 3 to 30 (e.g., about 5 to 10). The reflux ratio of the distillation column may be, for example, about 1 to 1000 (e.g., about 3 to 500), preferably about 5 to 100 (e.g., about 10 to 70), and more preferably about 15 to 50 (e.g., about 15 to 30).

The overhead stream (8A) or a condensate thereof (lines 83, 84, 85) is rich in acetaldehyde and methyl iodide. The condensate of the overhead stream (8A) may have an acetaldehyde concentration of, for example, about 1 to 70% by weight (e.g., about 10 to 65% by weight) and preferably about 30 to 60% by weight (e.g., about 35 to 55% by weight). The condensate may have a methyl iodide concentration of, for example, about 20 to 80% by weight (e.g., about 30 to 75% by weight) and preferably about 40 to 65% by weight (e.g., about 45 to 60% by weight). The condensate may have a methyl acetate concentration of, for example, about 0.01 to 20% by weight (e.g., about 0.1 to 15% by weight) and preferably about 1 to 10% by weight (e.g., about 2 to 8% by weight). The condensate of the overhead stream (8A) may have an acetic acid concentration of, for example, about 0 to 5% by weight, preferably about 0 to 3% by weight, and more preferably about 0 to 1% by weight, or may have an acetic acid concentration substantially not more than detection limit. The condensate may have a water concentration of, for example, about 0 to 10% by weight (e.g., about 0.01 to 8% by weight) and preferably about 0.1 to 5% by weight (e.g., about 0.3 to 3% by weight).

The condensate of the overhead stream (8A) may have a dimethyl ether concentration that can be selected from a wide range of about 10 ppm to 80% by weight, and may have a dimethyl ether concentration of, for example, about 100 ppm to 60% by weight (e.g., about 0.5 to 50% by weight) and preferably about 1 to 40% by weight (e.g., about 5 to 30% by weight). The concentration of dimethyl ether in the overhead stream (8A), which varies depending on process conditions, may be increased in some cases.

The overhead stream (8A) (the reflux line 83) may have a temperature at an atmospheric pressure of, for example, about 10 to 90° C. (e.g., about 15 to 80° C.) and preferably about 20 to 70° C. (e.g., about 20 to 65° C.). The condensate (lines 84, 85) of the overhead stream (8A) cooled in the condenser C6 may have a temperature of, for example, about 0 to 45° C. (e.g., about 3 to 35° C.) and preferably about 5 to 30° C. (e.g., about 7 to 25° C.).

The bottom liquid stream or aqueous bottom stream (8B) (line 81) usually contains water a main component and may contain acetaldehyde. The liquid stream (8B) may have an acetaldehyde concentration (on the basis of weight) of, for example, about 1 to 50% by weight (e.g., about 5 to 45% by weight) and preferably about 10 to 40% by weight (e.g., about 20 to 40% by weight). The liquid stream (8B) may have a methyl iodide concentration of, for example, not more than 1% by weight (e.g., about 1 ppm to 0.8% by weight), preferably not more than 0.5% by weight (e.g., about 0.001 to 0.2% by weight), and more preferably not more than 0.005 to 0.15% by weight. The liquid stream (8B) may have a methyl acetate concentration of, for example, about 1 ppm to 5% by weight (e.g., about 50 ppm to 2% by weight) and preferably about 0.01 to 1.5% by weight (e.g., about 0.05 to 1% by weight). The liquid stream (8B) may have an acetic acid concentration of, for example, not more than 5% by weight (e.g., about 1 ppm to 3% by weight) and preferably not more than 1% by weight (e.g., about 50 ppm to 0.5% by weight), or may have an acetic acid concentration substantially not more than detection limit (0% by weight). The liquid stream (8B) may have a water concentration of, for example, about 40 to 90% by weight (e.g., about 50 to 85% by weight) and preferably about 55 to 80% by weight (e.g., about 60 to 80% by weight). The liquid stream (8B) may have a dimethyl ether concentration of, for example, about 0 to 2% by weight (e.g., about 0.0001 to 1.5% by weight), preferably about 0.001 to 1% by weight (e.g., about 0.01 to 0.5% by weight), and more preferably about 0.1 to 0.5% by weight.

The bottom liquid stream or aqueous bottom stream (8B) may have a temperature at atmospheric pressure of, for example, about 15 to 110° C. (e.g., about 20 to 100° C.) and preferably about 25 to 80° C. (e.g., about 30 to 70° C.).

The scope of the present invention should not be limited to the process as shown in FIG. 1. As described above, various changes and modifications of the process unit and/or the process flow may be made. Hereinafter, typical modified embodiments will be explained. However, the scope of the present invention should not be limited to these modified embodiments.

(Liquid-liquid Separation of Condensable Gaseous Phase)

In the liquid-liquid separation step (4), a gas (off-gas) containing at least acetaldehyde and methyl iodide produced from the process may be condensed to separate the gaseous phase into two liquid phases, and the gas produced from the process includes, for example, a gaseous phase (overhead) that produced from at least one step selected from the group consisting of the reaction step (1), the flash evaporation step (2), the first distillation step (3), and the succeeding distillation steps (5), (7) and (8) [e.g., at least the first distillation step (3)].

(Plurality of Condensation Steps)

Among acetic acid, methyl acetate, methyl iodide, methanol, water, acetaldehyde, or other compounds, acetaldehyde has a boiling point close to that of methyl iodide and has the lowest boiling point. Thus, in the liquid-liquid separation step (4), in a case where the first overhead stream (3A) is cooled stepwise in a plurality of condensers (a plurality of condensers successively lower in cooling temperature) to form a plurality of condensates successively lower in temperature, a condensate formed by a subsequent condenser has a higher concentration of acetaldehyde, which is a lower boiling point component, compared with a process liquid (a condensate) formed by a first condenser. Moreover, in a case where the first overhead stream (3A) is cooled stepwise in such a plurality of condensers, in the first condenser the first overhead stream (3A) is separable into a first condensate and a first gas fraction (noncondensable fraction) having a high acetaldehyde concentration, in a second condenser the first gas fraction is separable into a second condensate having a high acetaldehyde concentration and a second gas fraction (noncondensable fraction). Accordingly, a condensate having a high concentration of acetaldehyde may be fed to the second distillation step (5) to separate acetaldehyde from the condensate.

The gas fraction (noncondensable fraction) in the condenser(s) may be fed as a vent gas or off-gas (exhaust gas) to an absorption system to further collect or recover a useful component such as methyl iodide.

(Water Extraction and Liquid-Liquid Separation)

The process shown in FIG. 1 may further comprise, in addition to the liquid-liquid separation step (4), an water extraction step for bringing the first overhead stream (3A) to contact with water [or subjecting the first overhead stream (3A) to water extraction] to separate the first overhead stream (3A) into an organic phase rich in methyl iodide and an aqueous phase rich in acetaldehyde. In the extraction step, the first overhead stream (3A) may be brought to directly contact with water to give an acetaldehyde extract and may optionally be separated into an aqueous phase and an organic phase. In order to improve the extraction efficiency, the aqueous phase and/or the organic phase separated in the liquid-liquid separation step (4) may be brought to contact with water to form an acetaldehyde extract. The aqueous phase and/or the organic phase formed by the water extraction may be subjected to the distillation step (5). In practical embodiments, the organic phase, which is rich in methyl iodide, may be subjected to the distillation step (5). The aqueous phase, which is rich in acetaldehyde, may be used as an extractant for the second distillation step (5) in the process shown in FIG. 2 as described later or may be fed to a concentration zone between the top of the column (the zeroth plate when the uppermost plate is the first plate) and a plate that is one plate upper than the side-cut stream (5B) (or side-cut plate).

(Combination of Distributive Distillation (or Azeotropic Distillation) and Extractive Distillation)

In one embodiment, the present invention may comprise the second distillation step or distributive distillation step (5) of transferring or distributing water in the first mixture to the upper stream (5A)(5B) predominantly than the lower stream or bottom stream (5C) by distillation, and the liquid-liquid separation step (6) of withdrawing the upper stream (5A) (5B) to separate the upper stream into two phases. The second distillation step (distillation column) (5) may comprise adding water and distilling the first mixture or first overhead stream (3A). The amount to be added of water is preferably in a range in which water does not apply an excessive load to the process, and may be small. Specifically, according to one embodiment of the present invention, the distributive distillation (or azeotropic distillation) may be carried out in parallel with the extractive distillation with water, that is, the extractive distillation may be carried out by addition of water while the distributive distillation (or azeotropic distillation) being carried out. For example, in the distributive distillation (or azeotropic distillation), the concentration efficiency of PRC's in the aqueous phase can further be increased by the extractive distillation, in which an extractant (e.g., water) is fed to the distillation column in addition to distillation; this broadens the operability of the process.

In such an embodiment, usually, for example, the extractant (e.g., water) may be added to an upper part of the distillation column (in particular, a concentration zone containing concentrated PRC's and methyl iodide in the distillation column) via the line 50, an extraction mixture (falling liquid) falling from the concentration zone may be withdrawn as the side-cut stream (5B) to form an aqueous phase and an organic phase, the aqueous phase alone may be removed to the outside of the system, and the organic phase may be recycled to the distillation column.

The process shown in FIG. 2 is substantially the same as the process shown in FIG. 1 except the second distillation step (5) and the liquid-liquid separation step (6). In the second distillation step (5), PRC's and methyl iodide are separated from each other by combination of the distributive distillation (or azeotropic distillation) and extractive distillation. Specifically, in the second distillation step (distillation column) (5), the first overhead stream (3A) fed via the feed line 43b and/or 44 [in the embodiment illustrated, the condensate from the liquid-liquid separation step (4)] is distilled to form a concentration zone [a zone with high concentrations of PRC's (in particular, acetaldehyde) and methyl iodide] in an upper part or zone of the distillation column: at least a portion of water in the first overhead stream (3A) is allowed to rise to the concentration zone; an extractant (water) capable of effectively extracting PRC's (in particular, acetaldehyde) relative to methyl iodide is added to the concentration zone via the line 50; and the extraction mixture (liquid, falling liquid) falling from the concentration zone is withdrawn as a side-cut stream (5B) from the distillation column. The withdrawn extraction mixture contains at least one PRC (in particular, acetaldehyde) effectively extracted with not only the water transferred or raised to the concentration zone but also the added extractant (water), and has a PRC's (in particular, acetaldehyde) concentration significant higher than the first overhead stream or first mixture (3A) fed to the distillation column (5) and the bottom stream (5C), and thus withdrawing the extraction mixture as the side-cut stream (5B) enables PRC's to be separated or removed effectively.

The distillation column of the distillation step (5) may be provided with a receiving or holding unit, for example, a receiver (e.g., a chimney tray) (51); the unit permits the upward transfer of the vapor or evaporation fraction of the first overhead stream (3A) [in the embodiment illustrated, the condensate from the liquid-liquid separation step (4)] to the concentration zone and the holding of the whole amount of the extraction mixture (or falling liquid) falling from the concentration zone. Incidentally, the extraction mixture may be liquid-liquid separable in a receiving unit capable of receiving the falling liquid as a mixture of the raffinate (methyl iodide liquid) and the extract.

The receiver is disposed at an upper position than the feed port of the first overhead stream (3A) and a lower position than the addition port of the extractant. The receiver (e.g., a chimney tray) has a usual structure, for example, a tray capable of receiving the extraction mixture (liquid, falling liquid) falling from the concentration zone, and hollow cylindrical chimneys; each chimney projects or extends from the edge of the opening of the tray toward the top of the column (upwardly), and allows the vapor or evaporated fraction of the first overhead stream (3A) to rise or transfer to the concentration zone. The chimney has an upper opening to which a cover (a cowl or a cap) is attached; the cover permits the vapor or evaporation fraction to move upward or pass through. The receiver (e.g., a chimney tray) may be provided with a withdrawing port or withdrawing line for withdrawing a liquid in the tray. The structure of the receiver (e.g., chimney tray) is not limited to the structure described above. The chimney, if necessary the cover, may have a small pore permitting the vapor or evaporation fraction to pass through. The tray may have a funnel structure, a curved structure, or other structures. The receiver (chimney tray) may have an opening ratio (an area ratio of the openings relative to the whole surface of the tray) of about 5 to 90%, for example, about 10 to 50% (e.g., about 15 to 40%), and preferably about 15 to 35%.

In the distillation column (5) provided with such a unit or receiver (chimney tray), the extractant (e.g., water) may be or may not be added to the concentration zone formed above the receiver. The concentration zone is formed in a space between the feed port and the top of the column. Due to a low boiling point of acetaldehyde and that of methyl iodide, the concentration zone can be formed in an upper space (the top side of the column), in particular, a space close to the top of the column. Thus, the receiver (e.g., a chimney tray) may be disposed at an upper position of the distillation column (5). The PRC's are extracted efficiently by withdrawing the side-cut stream (5B) from the concentration zone, and thus the position of the receiver [the position of a port withdrawing the side-cut stream (5B)] is upper than the feed port of the first mixture (3A) in practical embodiments. The receiver [a port withdrawing the side-cut stream (5B)] is not limited to a particular position, and may be disposed at the same height level as the height level of the feed port (or feed plate) of the first overhead stream or mixture (3A) or may be disposed at a recovery zone lower than the feed port. Specifically, the height level of the receiver may be the same as that of the feed port of the first overhead stream or first mixture (3A) or may be higher or lower than that of the feed port of the first mixture (3A). In a case where the receiver is disposed at a position lower than the feed port of the first overhead stream or first mixture (3A), the receiver may be positioned at an upper than the bottom stream.

According to the number of plates of the distillation column, the height level of the receiver (e.g., a chimney tray) is between the uppermost plate of the column (the 1st plate from the top of the column) and a plate at least one plate upper than the feed part or feed tray of the first overhead stream (3A) or is the top (or head) of the column. Assuming that the total number of plates of the distillation column is 100, the position (height level) of the receiver may correspond to about the 2nd to the 60th plate (e.g., about the 2nd to the 45th plate), preferably about the 2nd to the 30th plate (e.g., about the 2nd to the 25th plate), and more preferably about the 2nd to the 10th plate (e.g., about the 2nd to the 7th plate) from the top of the distillation column. For example, in a case where the distillation column is a plate distillation column having a total actual number of plates of 43, the receiver (e.g., a chimney tray) may be disposed in place of a plate between the uppermost plate of the top of the column (the 1st plate from the top of the column) or the top of the column and a plate that is positioned at at least one plate upper than the feed part or feed tray of the first overhead stream (3A) (for example, a plate that is at least 5 plates upper than the feed tray); or the receiver (e.g., a chimney tray) may be disposed in place of a plate between the uppermost plate of the top of the column and a plate that is positioned at 25 plates lower than the uppermost plate (the 25th plate) (preferably the 10th plate from the uppermost plate, more preferably the 5th plate from the uppermost plate, and particularly the 3rd plate from the uppermost plate). More specifically, the side-cut plate (receiver) of the side-cut stream (5B) may be positioned at the uppermost plate of the distillation column (the 1st plate), the 2nd or the 3rd uppermost plate (in particular, the uppermost plate or the 2nd uppermost plate).

The extractant can usually be added to the upper part of the distillation column (5) [for example, to the uppermost plate of the column, or between the top of the column and a plate that is positioned at one plate upper than the feed part or feed tray of the first overhead stream (3A)]. Assuming that the distillation column has a total number of plates of 100, the feed plate of the extractant may be about the 0th to the 50th plate (e.g., about the 1st to the 25th plate), preferably about the 1st to the 20th plate (e.g., about the 1st to the 15th plate), and more preferably about the 1st to the 10th plate from the top of the distillation column. For example, in a case where the distillation column is a plate distillation column having a total actual number of plates of 43, the extractant may be added to a plate close to the top of the distillation column (5) (e.g., the 0th to the 20th plate, preferably the uppermost to the 10th plate, more preferably the uppermost to the 5th plate, and particularly the uppermost to the 3rd plate). In order to increase the extraction efficiency by countercurrently adding the extractant to the rising vapor or evaporation fraction, the extractant may usually be added to the uppermost plate of the distillation column (5). In order to increase the extraction efficiency, the extractant can be added in a droplet form, in particular, may be added by spraying or sprinkling. The extractant may have a temperature of, for example, about 0 to 60° C., preferably about 10 to 50° C., and more preferably about 20 to 40° C., or may have an ordinary temperature (e.g., about 15 to 25° C.). The extractant may be added as an extractant warmed or heated (for example, heated to about 30 to 150° C. and preferably about 50 to 110° C.) or in the form of vapor (including superheated vapor).

The extractant is capable of effectively extracting PRC's (in particular, acetaldehyde) than methyl iodide. The extractant is preferably separable from the methyl iodide phase by liquid-liquid separation. Specifically, the preferred extractant can separate the extraction mixture (5B) into an upper phase and a lower phase. In particular, the extractant preferably includes an aqueous extractant containing at least water, for example, water, and a mixed solvent containing water and a water-soluble organic solvent [e.g., an alcohol (a monool) such as methanol, a glycol such as ethylene glycol, a polyhydric alcohol such as glycerin, acetone, an ester, and an ether]. Among these extrantants, water is preferred. Feeding water as the extractant keeps or maintains the extraction mixture (or droplet extraction mixture) in a liquid-liquid separated state to advantageously separate the extraction mixture into two phases.

The extractant may contain water and at least one component selected from the group consisting of PRC's, methyl iodide, acetic acid, methyl acetate, dimethyl ether, and a component present in the process (all components including the impurities described above). Such an extractant may be an aqueous solvent produced in the process [for example, an aqueous phase 43a produced in the liquid-liquid separation step (4) of the first overhead stream (3A), an aqueous process stream such as the extracts 62, 67, and 69 produced in the second liquid-liquid separation step (6) (e.g., an acetaldehyde-containing aqueous process stream), and other acetaldehyde-containing aqueous process streams (e.g., an aqueous phase formed by extracting PRC's with water)]. The extractant may also include an aqueous solution (for example, an aqueous solution containing acetaldehyde and methyl iodide) obtainable by absorption-treating an off-gas with water, the off-gas being produced from the process. The off-gas may include, for example, off-gases produced in a variety of unit operations in the process, such as off-gases produced in the reactor (1), the flash evaporator (2), the first distillation column (3), the second distillation column (5) or the separation unit 6a, the third distillation column (7), the fourth distillation column (8), or others.

In the process, not the whole of the distillation column but a space (or zone) between the addition port or part of the extractant and the receiver (side-cut part) can be used as an extraction space (an extraction zone); the vapor or vaporized fraction in the concentration zone (in particular, at least acetaldehyde and methyl iodide) can be extracted with water rising to the concentration zone and the added extractant. Thus PRC's (in particular, acetaldehyde) can be extracted efficiently with a smaller amount of the extractant relative to the amount of the extractant used for a process withdrawing the extraction mixture (5B) as the bottom stream (5C). For example, the weight ratio of the flow rate of the extractant relative to the flow rate of the first overhead stream (3A) (in terms of liquid stream) [the former/the latter] may be selected from a range of about 0.0001/100 to 100/100 (e.g., about 0.001/100 to 50/100) or may usually be about 0.0001/100 to 20/100 (e.g., about 0.001/100 to 10/100), preferably about 0.01/100 to 8/100, and more preferably about 0.1/100 to 5/100. Thus the extraction mixture or the falling liquid [or the side-cut stream (5B)] in the distillation column forms a liquid stream [or side-cut stream (5B)] having a low extractant content; the biphasically separable liquid stream forms an aqueous phase (a small amount of an aqueous phase or extract) and an organic phase (a large amount of an organic phase or raffinate).

Incidentally, according to the conventional combination of acetaldehyde-removing distillation with water extraction, a PRC-concentrated organic phase (or methyl iodide phase) is extracted with substantially the same amount of an extraction water as the PRC-concentrated organic phase. In contrast, according to one embodiment of the present invention, the amount of the extraction water is about 0.1% to 10% of the organic phase. Thus, in a case where the concentration of PRC's in the organic phase is substantially the same, the concentration of PRC's in the aqueous phase can significantly be increased compared with the conventional water extractive distillation. In other words, PRC's can be extracted with water efficiently even if the organic phase has a low PRC's concentration, and thus the separation zone (the actual number of plates or the theoretical number of plates) of the distillation column may be reduced compared with the conventional art, removing acetaldehyde with a lower cost. Meanwhile, irrespective of the amount of the organic phase, the organic phase has a high (substantially equivalently high) methyl iodide concentration; under the same acetaldehyde (AD) concentration in the aqueous phase, the concentration of methyl iodide (MeI) dissolved in the aqueous phase is low and is hardly changed regardless of the amount ratio of the aqueous phase and the organic phase after the extraction. Thus even though an extremely smaller amount of the extractant relative to the amount of the organic phase to be extracted is used, the ratio (MeI/AD ratio) of methyl iodide (MeI) relative to acetaldehyde (AD) can be reduced effectively compared with the conventional combination of the acetaldehyde-removing distillation with water extraction, and PRC's can be removed effectively under the condition of reducing a loss of methyl iodide to the outside of the system with a small distillation zone and a low cost.

Incidentally, Examples of PTL 2 (TABLE 2) disclose that, in water extractive distillation using a second distillation column, water is fed to a top of the column, a feed liquid having an acetaldehyde concentration of 31% by weight is distilled in the column, and an aqueous bottom stream is withdrawn from a bottom of the column, and that the acetaldehyde concentration of 31% by weight in the feed liquid is reduced to 22.4% by weight in the bottom stream. However, the water extractive distillation described in PTL 2 requires 100 or more times the amount of the extractant that the second distillation step (5) according to one embodiment of the present invention. Incidentally, according to one embodiment of the present invention, methyl iodide can be withdrawn as the overhead stream or first mixture (3A) from a side the distillation column (5), whereas according to PTL 2, methyl iodide is mainly withdrawn from the top of the column; both are quite different in separation manner of methyl iodide. According to one embodiment of the present invention, a bottom stream having a high methyl iodide concentration is obtainable by withdrawing the side-cut stream from the distillation column (5) and returning the withdrawn stream to the distillation column (5). If, in accordance with the process of PTL 2, the amount of the extractant (e.g., water) fed to the top of the distillation column is 100 or more times as large as that of the extractant in one embodiment of the present invention (for example, the amount of the extractant is substantially the same as or larger than the amount of the feed liquid), the ratio of the bottom rate/the feed rate in accordance with PTL 2 is 100 or more times as high as the side-cut aqueous phase rate/feed rate in one embodiment of the present invention. Thus, in a case where the bottom aqueous stream is directly discharged to the outside of the system or is further distilled for separation of acetaldehyde and methyl iodide from water, at least 5 to 10 or more times the amount of methyl iodide is discharged to the outside of the system in comparison with one embodiment of the present invention due to methyl iodide dissolved in the bottom stream (aqueous stream). Moreover, differently from the present invention, according to PTL 2, most of feed methyl iodide is withdrawn from the top of the column, and thus a large amount of energy is required, which is uneconomic.

Further, since the extraction mixture not as the bottom stream or bottom stream (5C) but as the side-cut stream (5B) is withdrawn from a withdrawing port of a receiver (e.g., a chimney tray), PRC's (in particular, acetaldehyde) and methyl iodide can be separated from each other even if the number of plates of the distillation column is significantly decreased. For example, assuming that the total number of plates of the distillation column is 100, the number of plates of the distillation column in one embodiment of the present invention can be reduced to about 10 to 80 (preferably about 12 to 60, more preferably about 15 to 50, and particularly about 20 to 40).

In a case where a membrane separation of PRC's and methyl iodide is further conducted following the extractive distillation in the distillation column (5), assuming that the total number of plates of the distillation column (5) is 100 as the same as that of the distillation column of PTL 2, the number of plates of the distillation column in one embodiment of the present invention can be reduced to about 5 to 20. For example, in a case where an aqueous phase having a higher methyl iodide/PRC's ratio than a process stream prior to the PRC's removal is withdrawn in the extractive distillation step by the distillation column (5) and then PRC's are separated from the withdrawn phase in a succeeding step (e.g., membrane separation), the number of plates of the distillation column (5) can further significantly be reduced as described above.

From the distillation column, at least a portion of the extraction mixture (5B) is withdrawn. In practical embodiments, the extraction mixture retained in the tray may be withdrawn continuously. Specifically, the extraction mixture can be withdrawn from the distillation column depending on the amount of the liquid falling from the concentration zone (the whole amount of the falling liquid).

In the process shown in FIG. 2, the second mixture (for example, an azeotropic mixture) forming the concentration zone may have a composition corresponding to a composition of the side-cut stream (5B) (a mixture of an aqueous phase and an organic phase when the stream is separated into these phases; a mixture in the line 63); or a composition depending on a composition of the second overhead stream (5A), a composition of the side-cut stream (5B) and a flow rate ratio of these streams.

The side-cut stream (5B) contains PRC's such as acetaldehyde, methyl iodide, methyl acetate, acetic acid, water, dimethyl ether, or other components; each component has a concentration similar to the corresponding concentration in each of the mixture (the mixture in the line 63), the separated aqueous phase, and the separated organic phase as described above. A temperature of the side-cut stream (5B) (line 63) is as described above.

Further, in the liquid-liquid separation step (6) of the embodiment shown in FIG. 2, the second overhead stream (5A) is cooled and condensed in the condenser C3 on the withdrawing line 53 and is then biphasically separated in the separation unit (decanter) 6a to form an organic phase (a lower phase, a raffinate) and an aqueous phase (an upper phase, an extract). The organic phase is recycled, for reflux, to the distillation column (for example, the top of the column) of the second distillation step (5) via the reflux line 61. The aqueous phase from the decanter 6a is fed to the hold tank 6b via the line 62. The extraction mixture (5B) as the side-cut stream is also fed to the hold tank 6b via the line 63. The liquid in the hold tank 6b is biphasically separated. The hold tank 6b also functions as a buffer tank or a decanter.

The organic phase (the raffinate) from the hold tank 6b is recycled to the distillation column of the second distillation step (5) via a line 64 and a recycle line 65 at a position lower than a position withdrawing the side-cut stream (5B) from the distillation column. The side-cut stream and extraction mixture (5B) have a relatively high temperature, and a portion of the aqueous phase (the extract) from the hold tank 6b is cooled in a cooling unit (cooler) C4 on the line 66 and is biphasically separated in the decanter 6c. The residual portion of the aqueous phase (the extract) from the hold tank 6b is recycled to the distillation column of the second distillation step (5) via the line 67 at a position lower than a position withdrawing the side-cut stream (5B) from the distillation column. As shown by a dotted line in FIG. 2, a portion of the aqueous phase (extract) in the line 66 may be recycled as an extractant.

In the decanter 6c, a small amount of methyl iodide can be separated by biphasic separation (or formation of an organic phase and an aqueous phase). The organic phase (a heavy phase rich in methyl iodide or a lower phase) formed in the decanter 6c is recycled to the distillation column of the second distillation step (5) via the line 68. The aqueous phase (a light phase rich in acetaldehyde or an upper phase) formed in the decanter 6c is fed to the third distillation step (distillation column) (7) via the line 69 for further separating PRC's and methyl iodide. As described above, in this embodiment, with respect to the side-cut stream (extraction mixture) (5B), a portion of the aqueous phase formed in the hold tank 6b and the organic phases (the organic phase formed in the hold tank 6b and the organic phase formed in the decanter 6c) are mixed together via the line 67 and the lines 64, 68, respectively, to recycle the mixture to the second distillation step (5).

In the process shown in FIG. 2, the miscible solvent is usually fed to an intermediate or lower position or part [a position lower than a receiver (e.g., a chimney tray)] of the distillation column in height level in order to prevent methyl acetate concentrating in a space between the lower feed port and the feed plate of first overhead stream (3A) [a condensate from the liquid-liquid separation step (4)] in practical embodiments. The miscible solvent may be fed to an upper position or part than the intermediate of the distillation column in height level [an upper position or part (e.g., a concentration zone or an extraction zone) than a receiver (e.g., a chimney tray) or above a receiver].

In the process shown in FIG. 2, assuming that the total number of plates of the distillation column is 100, feeding the miscible solvent (such as acetic acid) to a plate lower than the recycle line 65 (for example, a plate that is positioned at 10 to 30 plates lower than a recycle plate to which a recycle stream is fed via the recycle line 65 can effectively prevent the miscible solvent (e.g., acetic acid) from mixing with the extraction mixture (5B) of the line 63. Thus, it is possible to reduce the amount of methyl iodide dissolved in the aqueous phase separated in the liquid-liquid separation step (6). Assuming that the total number of plates of the distillation column is 100, the miscible solvent such as acetic acid may be fed to a plate that is lower than the side-cut plate (receiver) of the side-cut stream (5B) and is the 10th to the 50th (e.g., the 20th to the 40th) plate from the uppermost plate.

The total of the amount of the extraction mixture (5B) recycled to the distillation step (5) [for example, the recycled amount of the aqueous phase, biphasically separated, in the extraction mixture (5B)] and/or the added amount of the miscible solvent may be not more than 30% by weight [e.g., about 0.01 to 20% by weight (e.g., about 0.1 to 15% by weight) and preferably about 0.5 to 10% by weight (e.g., about 1 to 5% by weight)] relative to the amount of the liquid falling from the concentration zone in the distillation step (5), as the same as described above.

In the above-mentioned distributive distillation (or combination of the distributive distillation and the extractive distillation), even if the first overhead stream (3A) contains an amphipathic component (such as methyl acetate or acetic acid) having an affinity with both PRC's (such as acetaldehyde) and methyl iodide, the PRC's (such as acetaldehyde) in the first overhead stream (3A) can effectively be extracted to the upper stream (5A)(5B), and thus the PRC's (such as acetaldehyde) can be separated and removed. For example, the acetaldehyde concentration of the upper stream (5A)(5B) is higher than that of the first overhead stream (3A) and that of the bottom stream (5C). For example, each of the concentration of PRC's (such as acetaldehyde) in the second overhead stream (5A) [the aqueous phase of the second overhead stream (5A)] and that in the side-cut stream (5B) [the aqueous phase of the side-cut stream (5B)] is about 10 to 1000 times (e.g., about 20 to 800 times), preferably about 30 to 500 times (e.g., about 50 to 200 times), more preferably about 50 to 170 times (e.g., about 60 to 150 times) as large as that in the first overhead stream (gaseous stream or a condensate stream thereof) (3A).

The ratio of acetaldehyde relative to methyl iodide in the upper stream (5A)(5B) is higher than that in the first overhead stream (3A) and is higher than that in the bottom stream (5C).

(Liquid-liquid Separation Step (6))

The upper stream (5A) and the upper stream (5B) may biphasically be separated independently or in combination of the upper stream (5A) and the upper stream (5B). Specifically, as described above, each of the overhead stream (5A) and the side-cut stream (5B) may be liquid-liquid separated; or, without liquid-liquid separation of the overhead stream (5A), the overhead stream (5A) may mix with the side-cut stream (5B) in the decanter 6a and the mixture may be liquid-liquid separated.

The liquid-liquid separation step (6) may comprise one or two liquid-liquid separation steps (or a hold tank and/or a decanter) without using a plurality of units (the separation unit 6a, the hold tank 6b, and the decanter 6c). For example, in the second liquid-liquid separation step (6) of the process as shown in FIG. 2, the separation unit 6a is not necessarily needed. For example, as shown in FIG. 3, the overhead stream (5A) from the distillation step (5) is cooled and condensed in the condenser C3, and the whole of the condensate is refluxed in the distillation column (5) using a reflux unit 106 instead of the separation unit 6a. As shown in FIG. 4, in the process similar to the process shown in FIG. 3, the side-cut stream (5B) may be fed to the decanter 6c via the cooling unit (cooler) C4 without passing through the hold tank 6b, and a portion 69a of the aqueous phase (the light phase rich in acetaldehyde or the upper phase) (the line 69) may be mixed with the organic phase (the line 68) for recycling the resulting mixture to the second distillation step (5) via the recycle line 65. For refluxing the whole of the overhead stream (5A), the reflux unit 106 is not necessarily needed. The second liquid-liquid separation step (6) does not necessarily require a plurality of liquid-liquid separation units 6b and 6c. The second liquid-liquid separation step (6) may use a single liquid-liquid separation unit (such as a tank, a decanter, a hold tank, or a buffer tank).

At least a portion of the aqueous phase (acetaldehyde-enriched aqueous phase) produced in the liquid-liquid separation step (6) may be removed to the outside of the process, or may be recycled to the reaction step (reactor) (1), or may be used as an extractant for the distillation step (5) in the process as shown in FIG. 2, FIG. 3, or FIG. 4. The aqueous phase [e.g., an extract from the extraction mixture (5B)] and/or the organic phase [e.g., a raffinate from the extraction mixture (5B)] produced in the step (6) may be recycled in various forms (via various routes) to the second distillation step (5). At least a portion of the organic phase (an organic phase containing methyl iodide) may be recycled to the distillation step (5) directly or indirectly. For example, the organic phase rich in methyl iodide can be recycled to an appropriate position of the distillation column of the second distillation step (5), may be recycled to an upper position than the withdrawing port for the upper stream (5A)(5B), or may preferably be recycled to a lower position than the withdrawing port for the upper stream (5A)(5B) to form a second mixture (or concentrated mixture) in the second distillation step (5). For example, as shown in FIG. 4, the portion 69a of the aqueous phase (the light phase rich in acetaldehyde or the upper phase) (the line 69) may be mixed with the organic phase (the line 68) for recycling the resulting mixture to a lower position than the withdrawing port for the upper stream (5A)(5B) of the second distillation column (5) via the recycle line 65. To the second distillation step (5) may be recycled a portion of the organic phase (or raffinate), practically at least a portion of the organic phase (or raffinate), for example, the whole of the organic phase (or raffinate).

Recycling at least the aqueous phase to a feed port (or a feed plate) being in a lower position of the distillation column (5) than port(s) for withdrawing the upper stream (5A)(5B) increases the concentrations of acetaldehyde and water in an upper position than the feed plate in the distillation column (5), thus forming an azeotropic composition containing combination of a plurality of components such as methyl iodide, acetaldehyde, and water, and in some cases reducing the concentration of acetic acid by increasing the water concentration. In such recycle of the aqueous phase, formation of an azeotrope containing no methyl acetate reduces the concentration of methyl acetate in a space upper than the feed plate of the distillation column (5). Further, in such cases, acetic acid present in the distillation column (5) is converted into methyl iodide or methyl acetate in a space upper than the feed plate of the distillation column (5), thus decreasing in concentration. For example, the concentration of methyl acetate or acetic acid in a space upper than the feed plate (recycle plate) of the distillation column (5) can be reduced: by feeding the aqueous phase and the organic phase to the distillation column (5) via the feed lines 43b and 44; recycling the organic phase via the lines 64, 68 and the aqueous phase via the line 67 to the distillation column (5); and/or feeding the aqueous phase to the distillation column (5) via the feed line 43b. Moreover, recycling a stream (including an aqueous phase, an organic phase, or others) to the second distillation step (5) increases the concentration of the recycling stream in the distillation column and prevents an increase in the concentration of the amphipathic compound such as methyl acetate, irrespective of the position of the withdrawing port for withdrawing the upper stream (5A)(5B). Thus, the concentration of methyl acetate or acetic acid in the aqueous phase [for example, the overhead stream (5A) or the side-cut stream (5B), the aqueous phase in the tank 6b, and further, the aqueous phase via the line 67] can be reduced to decrease the amount of methyl iodide dissolved in the aqueous phase. The recycling amount of the aqueous phase may suitably be selected considering the stability of the process. Too large a recycling amount of the aqueous phase causes outflow of a large amount of water from the bottom stream (5C) (line 52) of the second distillation column (5) to undesirably increase the concentration of water in the reaction system or the process. In a case where a large amount of acetic acid mixes with the upper stream (5A)(5B) by addition and distillation and recycling of acetic acid (miscible solvent) as an amphipathic component, the amount of methyl iodide, as well as methyl acetate, dissolved in the aqueous phase is increased to induce a loss of methyl iodide.

In the process shown in FIG. 2, in a case where the extraction mixture (5B) is biphasically separable in the distillation column of the distillation step (5), the extraction mixture (5B) may biphasically be separated by retaining the extraction mixture (5B) in a tray (or a decanter in the system), or an aqueous phase formed in the column may selectively be withdrawn by side-cut. In a preferred embodiment, the whole amount of the falling liquid or the extraction mixture (5B) may be withdrawn from the distillation column of the distillation step (5) by side-cut, and if necessary after being cooled, the withdrawn mixture may biphasically be separated in a decanter which is disposed outside of the system.

In one embodiment of the process of the present invention, the total retention time of the second mixture in the distillation zone formed in the distillation column and the decanter disposed in the outside of the system (including a retention time in an extractive distillation zone formed in the distillation column, in the process shown in FIG. 2) may be sufficient for biphasically separating the second mixture. The total retention time may be, for example, not less than 10 seconds (e.g., about 30 seconds to 120 minutes) and preferably about 1 to 100 minutes (e.g., about 5 to 60 minutes), or may be about 10 to 120 minutes (e.g., about 15 to 60 minutes).

In the process shown in FIG. 2, it is not necessary to cool and condense the second overhead stream (5A) for liquid-liquid separating the condensate in the separation unit 6a. The whole of the second overhead stream (5A) may be refluxed in the distillation column of the second distillation step (5).

In the process shown in FIG. 2, as described above, the side-cut stream (5B) is practically obtained from concentration zone in order to extract PRC's efficiently. In such a case, the extraction mixture (such as the organic phase) may be recycled to the concentration zone of the distillation column (5) or may be recycled to a plate having the same height level as that of the feed port (or feed plate) for the first overhead stream or mixture (3A) or may be recycled to a plate lower than the feed port.

If necessary, the liquid (the condensate, the aqueous phase and/or the organic phase) formed in the liquid-liquid separation step (6) may temporarily be stored or retained in a buffer tank to reduce fluctuation of the flow rate of the process stream.

In the liquid-liquid separation step (6), the upper stream (5A) and/or the upper stream (5B) may biphasically be separated to further separate PRC's and methyl iodide from each other.

(Distillation Steps (7)(8))

Regardless of use of acetic acid as the miscible solvent, the upper stream (5A)(5B) as well as the succeeding process stream, for example, the condensate (the aqueous phase and/or the organic phase, in particular, the aqueous phase) from the liquid-liquid separation step (6) usually contain acetic acid and methyl acetate in addition to acetaldehyde and methyl iodide. Distilling the process stream containing such components in the above-mentioned third distillation step (7) distributes acetic acid or methyl acetate to the extractant (in particular, water) of the bottom liquid stream (7B) to separate acetaldehyde and methyl iodide from acetic acid. Specifically, the distillation column (7) allows efficient separation of acetic acid and methyl acetate from the process stream. Thus, at least a portion or the whole of the aqueous phase (or extract) formed in the second liquid-liquid separation step (6) is practically fed to the third distillation step (distillation column) (7). Further, water extractive distillation in the fourth distillation step (8) following the third distillation step (7) prevents methyl iodide from mixing in the bottom liquid stream (8B) due to an affinity between water and acetaldehyde to provide the bottom liquid stream or aqueous solution (8B) having an extremely high ratio (AD/MeI) of acetaldehyde (AD) relative to methyl iodide (MeI). Specifically, after acetic acid and methyl acetate are removed in the third distillation step (7) in addition to the second distillation step (5), further water extractive distillation is conducted in the fourth distillation step (8); this achieves energy saving and reduction of the cost of equipment in comparison with the conventional process, and in addition, reduces a discharge loss of methyl iodide to the outside of the system. The AD/MeI ratio in the bottom liquid stream or aqueous solution (8B) may be, for example, about 20/1 to 2000/1 (e.g., about 50/1 to 1500/1), preferably about 100/1 to 1000/1 (e.g., about 150/1 to 750/1), and more preferably about 200/1 to 500/1 (e.g., about 250/1 to 450/1).

If necessary, a portion of the organic phase (or raffinate) may be fed to the third distillation step (distillation column) (7).

By separating acetic acid or methyl acetate as the bottom liquid stream (7B), the third overhead stream (7A) from the third distillation step (7) has a reduced distributability or dissolubility of methyl iodide to water. Thus, if necessary, acetaldehyde may be extracted with water from the third overhead stream (7A) by one or a plurality of water extraction units provided with a mixer and a settler or by an extraction column, instead of the fourth distillation step (8).

The condensate (the aqueous phase and/or the organic phase, for example, the aqueous phase) from the liquid-liquid separation step (6) may be subjected to water extractive distillation in the fourth distillation step (8) without subjecting to the third distillation step (7). The upper stream (5A)(5B) or the fluid (such as the aqueous phase) from the second liquid-liquid separation step (6) may be distilled in the fourth distillation step (8). The third distillation step (7) and/or the fourth distillation step (8) are not necessarily needed.

The aqueous phase obtained by biphasically separating the upper stream (5A)(5B) also contains methyl iodide. Thus, at least a portion of the aqueous phase obtained by biphasically separating the upper stream (5A)(5B) is often subjected to water extraction in the extraction or extractive distillation step (8). Incidentally, the above aqueous phase and/or the overhead stream (7A) from the distillation step (7) may be subjected to water extraction in the extraction or extractive distillation step (8).

Instead of the fourth distillation step (8), an extraction unit (such as an extraction column or an extractor) may be used. An aqueous solvent produced in the process may be used as an extractant in the second distillation step (5).

(Impurities or Other Compounds in Process Stream)

As described above, each one of the process streams (e.g., a process stream, such as the first mixture (3A) or phases separated therefrom, or the upper stream (5A)(5B) or phases separated therefrom) usually contains other components (including impurities) inevitably. The process stream may have a methanol concentration of, for example, about 0 to 5% by weight (e.g., about 0.0001 to 3% by weight), preferably about 0.001 to 1% by weight (e.g., about 0.01 to 0.5% by weight), and more preferably about 0.1 to 0.5% by weight. The process stream may have a hydrogen iodide concentration of about 0 to 5000 ppm (e.g., about 1 to 1000 ppm) and preferably about 5 to 500 ppm (e.g., about 10 to 300 ppm). The process stream may have a concentration of each of formic acid and $C_{3-8}$alkanecarboxylic acids (such as propionic acid) of, for example, about 0 to 500 ppm (e.g., about 1 to 300 ppm) and preferably about 0 to 100 ppm (e.g., about 5 to 50 ppm). The process stream may have a concentration of each of acetaldehyde-derived aldehydes (such as crotonaldehyde and 2-ethylcrotonaldehyde) of, for example, about 0 to 500 ppm (e.g., about 1 to 300 ppm) and preferably about 0 to 100 ppm (e.g., about 5 to 50 ppm). The process stream may have a concentration of each of alkyl iodides ($C_{2-12}$alkyl iodides such as hexyl iodide) of, for example, about 0 to 100 ppm (e.g., about 1 ppb to 50 ppm) and preferably about 0 to 10 ppm (e.g., about 10 ppb to 5 ppm).

(Applicable First Mixture)

In the embodiments shown in FIG. 1 and FIG. 2, the first overhead stream (3A) (including a condensate thereof, and an aqueous phase and/or an organic phase liquid-liquid separated therefrom) corresponds to the first mixture (or mixture). The first mixture is not limited to the first overhead stream (3A) or a condensate thereof and may be any mixture containing at least one PRC (such as acetaldehyde), methyl iodide, and water, for example, a mixture produced from the reaction step (reaction system or reactor) (1), the flash evaporation step (flasher) (2), or the first distillation step (3); and a mixture produced from each one of steps following the second distillation step (5) [for example, the second liquid-liquid separation step (6), the third distillation step (third distillation column) (7), and the fourth distillation step (fourth distillation column) (8)]. In one embodiment of the present invention, PRC's (e.g., acetaldehyde) and methyl iodide can effectively be separated from each other even in such a first mixture (in particular, a first mixture containing methyl acetate).

In one embodiment of the present invention, the process is applicable to the first mixture or overhead stream containing at least one PRC and methyl iodide, in particular, a liquid-liquid (biphasically) separable first mixture or overhead stream, and is applicable for not only the second distillation column (5) but also one or a plurality of distillation columns following the first distillation column (3) to selectively separate PRC's by using extractive distillation in the concentration zone. In the first mixture or overhead stream, at least methyl iodide among permanganate reducing compounds (PRC's) and methyl iodide is concentrated, compared with a mixture stream produced in a preceding unit operation [for example, a stream fed to the first distillation column (3)]. The first mixture or overhead stream may also contain concentrated PRC's or may have a reduced concentration of water. The above unit operation may include one or a plurality of various unit operations, e.g., a flash step, a distillation step (including a water extractive distillation step), an extraction step, a condensation and liquid-liquid (biphasic) separation step, an absorption step, and a membrane separation step.

EXAMPLES

The following examples are intended to describe this invention in further detail and should by no means be interpreted as defining the scope of the invention.

The experimental results are shown below. In Examples and Comparative Example, an Oldershaw distillation column having a diameter of 40 mm was used as the second distillation column (5). In Examples, the second distillation step (5), the liquid-liquid separation step (6), and the separation unit 6a were provided according to the process shown in FIG. 1. Accordingly, the organic phase in the separation unit 6a was recycled to the distillation step (5) via the line 67, and the aqueous phase in the separation unit 6a is discharged via the line 66.

In a process of Comparative Example 1, a second distillation column (acetaldehyde-removing column) 206, an extraction column 207, and a distillation column 208 were used, as shown in FIG. 5.

In the following Comparative Example and Examples, numerical values were expressed as follows. Measured values were rounded off to the second last digit. With respect to the measured values in Comparative Example and Examples, concentration values were basically expressed as one decimal place, and flow rate values expressed were determined by rounding off measured values. In Tables, the concentration of each component was basically expressed as two decimal places; for a component having a lower concentration, the concentration was expressed as three or four decimal places. In Tables, the sum total of the concentrations of the components described is not strictly 100% by weight in some cases. In such cases, the amount of the component having the maximum concentration is used as a balanced amount so that the sum total was expressed as 100% by weight. The amount of the component having the maximum concentration was shown as a balanced amount "BL". In the balanced amount "BL", traces of impurities or other components are also contained.

Comparative Example 1

A second distillation column 206 having an actual number of plates of 100 [acetaldehyde-removing column: column top temperature of 22° C., column bottom temperature of 48° C., column top pressure of atmospheric pressure+10 mmH$_2$O (about 100 Pa)] was provided. To the 32th plate from the bottom of the distillation column 206, a feed liquid (temperature: 20° C.) was fed at 1295 g/h. An overhead 262 (temperature: 22° C.) produced by the distillation was cooled to 7° C. in a condenser C3. A portion of the condensate was refluxed at a rate of 987 g/h (via a reflux line 263), and the residual portion of the condensate was distilled off via a line 264 at a rate of 6.0 g/h. The feed liquid was a methyl iodide (MeI) solution having an acetaldehyde (AD) concentration of 1960 ppm, a methyl acetate (MA) concentration of 14.9% by weight, a water concentration of 0.7% by weight, and an acetic acid (AC) concentration of 1.9% by weight. The condensate (the line 264) of the overhead had an AD concentration of 41.4% by weight (MeI solution). The MeI solution was fed to a top of an extraction column 207 having a theoretical number of plates of 1 [column top temperature of 15° C., column bottom temperature of 15° C. absolute pressure of about 0.1 MPa (atmospheric pressure)] via the line 264, water (temperature: 15° C.) was fed at a rate of 6.0 g/h to a bottom of the extraction column 207 via a line 271, and a water extraction solution (temperature: 15° C.) having an AD concentration of 26.4% by weight was withdrawn at a flow rate of 8.5 g/h from a top of the column (a line 275). The AD-containing water extraction solution was fed to a distillation column (AD separation column) 208 (column top temperature of 21° C., column bottom temperature of 102° C., column top pressure of atmospheric pressure+10 mmH$_2$O) via a feed line 275 and distilled to form an overhead 282 having a temperature of 21° C. The overhead 282 was cooled in a condenser C6 to give a condensate (temperature: 7° C.). A portion of the condensate was refluxed at a rate of 25.3 g/h (via a reflux line 283), and the residual portion of the condensate, which had an AD concentration of 88.8% by weight and a MeI concentration of 10.8% by weight (temperature: 7° C.), was withdrawn at a flow rate of 2.53 g/h via a withdrawing line 284. From a bottom of the column, a bottom stream (temperature: 102° C.) was withdrawn via a line 281. According to the process, AD and MeI were removed from the process at a flow rate of 2.25 g/h and a flow rate of 0.27 g/h, respectively. The second distillation column (acetaldehyde-removing column) 206 required a reboiler heat quantity of 100.2 kcal/h, and the AD separation column 208 required a reboiler heat quantity of 4 kcal/h.

Table 1 shows componential analysis in each line depicted in FIG. 5.

TABLE 1

Composition in Line No. depicted in FIG. 5 (% by weight)

| Line No. | 44 | 261 | 262/263/264 | 272 | 275 | 282/283/284 |
|---|---|---|---|---|---|---|
| AD | 0.196 | 0.0038 | 41.39 | 6.79 | 26.39 | BL |
| MeI | BL | BL | BL | BL | 3.22 | 10.83 |
| MA | 14.89 | 14.96 | 0.33 | 0.37 | 0.08 | 0.26 |
| H$_2$O | 0.70 | 0.70 | 0.53 | 1.27 | BL | 0.14 |
| AC | 1.90 | 1.91 | 0.00 | 0.00 | 0.00 | 0.00 |
| Total | 100 | 100 | 100 | 100 | 100 | 100 |

In Table 1, AD indicates acetaldehyde, MeI indicates methyl iodide, MA indicates methyl acetate, and AC indicates acetic acid (the same applies hereinafter).

Example 1

A second distillation column 5 having an actual number of plates of 30 [column top temperature of 23° C., column bottom temperature of 47° C., column top pressure of atmospheric pressure+10 mmH$_2$O (about 100 Pa)] was provided. To the 7th plate from the bottom of the distillation column, a feed liquid (temperature: 20° C.) was fed at a rate of 1295 g/h. A vapor rising to a top of the column (an overhead) was cooled to 7C in a condenser C3 and was then biphasically separated in a decanter 6a into an aqueous phase and an organic phase (MeI phase). The organic phase alone from the decanter 6a was refluxed to the distillation column 5 at a reflux rate of 590 g/h. The aqueous phase alone was withdrawn at a rate of 12.5 g/h via a line 66, removing AD. The feed liquid used was a methyl iodide solution having an AD concentration of 2011 ppm, a MA concentration of 15.05% by weight, a water concentration of 1.1% by weight, and an AC concentration of 2.31% by weight. From a bottom of the distillation column, a bottom stream (temperature: 47° C.) was withdrawn at a rate of 1280 g/h via a line 52.

According to the process, AD and MeI in the aqueous phase (line 66) were removed from the process at a flow rate of 2.53 g/h and a flow rate of 0.23 g/h, respectively. The second distillation column 5 required a reboiler heat quantity of 49 kcal/h.

Table 2 shows the results of componential analysis in each line depicted in FIG. 1.

TABLE 2

Composition in Line No. depicted in FIG. 1 (% by weight)

| | Line No. | | | |
|---|---|---|---|---|
| | 44 | 52 | 61 | 66 |
| AD | 0.2011 | 0.0057 | 12.90 | 20.20 |
| MeI | BL | BL | BL | 1.80 |
| MA | 15.05 | 15.20 | 3.20 | 0.95 |
| H$_2$O | 1.10 | 0.366 | 0.10 | BL |
| AC | 2.31 | 2.34 | 0.00 | 0.00 |
| Total | 100 | 100 | 100 | 100 |

Table 3 represents the results of separation efficiency and energy efficiency in Comparative Example and Example 1.

TABLE 3

| | Number of distillation plates (plates) | Amount of AD removed (g/h) | Amount of MeI lost (g/h) | MeI/AD ratio | Reboiler Duty (kcal/h) | | | |
|---|---|---|---|---|---|---|---|---|
| | | | | | 2$^{nd}$ distillation column | 3$^{rd}$ distillation column | 4th distillation column | Total |
| Comparative Example 1 | 100 | 2.25 | 0.27 | 0.122 | 100.2 | 4.3 | — | 104.5 |
| Example 1 | 30 | 2.53 | 0.23 | 0.089 | 49 | — | — | 57 |

Examples 2 and 3

In the process shown in FIG. 4, the first overhead stream (3A) (the condensate from the liquid-liquid separation step (4)) was fed to a distillation column (5) having an actual number of plates of 10 via the line 44 without addition of water (Example 2) or with addition of water (Example 3) as an extractant via the line 50, and the side-cut stream (5B) was withdrawn. Any miscible solvent was not fed to the distillation column (5).

Tables 4 and 5 show the analysis results (material balance) of each component in each line shown in FIG. 4.

TABLE 4

(Example 2)
Composition in Line No. depicted in FIG. 4 (% by weight)

| Line No | 44 | 52 | 53 | C3 vent | 61 | 63 | 68 | 69(69a) | 65 |
|---|---|---|---|---|---|---|---|---|---|
| DME | 0.004 | 0.000 | 0.79 | 31.0 | 0.8 | 0.1 | 0.06 | 0.09 | 0.1 |
| AD | 0.185 | 0.017 | BL | BL | BL | 6.7 | 6.6 | 21.5 | 6.6 |
| MeI | BL | BL | 11.0 | 7.1 | 11.0 | BL | BL | 1.7 | BL |
| MeOH | 0.10 | 0.073 | 0.09 | 0.0 | 0.1 | 0.0 | 0.0 | 4.0 | 0.0 |
| MA | 14.1 | 14.2 | 0.5 | 2.4 | 0.5 | 3.9 | 3.9 | 1.8 | 3.9 |
| $H_2O$ | 0.73 | 0.24 | 0.1 | 0.0 | 0.1 | 0.8 | 0.13 | BL | 0.1 |
| AC | 2.01 | 2.0 | 0.0 | 0.0 | 0.0 | 0.0 | 0.0 | 0.0 | 0.0 |
| Total | 100.0 | 100.0 | 100.0 | 100.0 | 100.0 | 100.0 | 100.0 | 100.0 | 100.0 |

TABLE 5

(Example 3)
Composition in Line No. depicted in FIG. 4 (% by weight)

| Line No | 44 | 50 | 52 | 53 | C3 vent | 61 | 63 | 68 | 69(69a) | 65 |
|---|---|---|---|---|---|---|---|---|---|---|
| DME | 0.004 | 0.0 | 0.0 | 0.78 | 32.4 | 0.8 | 0.1 | 0.06 | 0.09 | 0.06 |
| AD | 0.185 | 0.0 | 0.029 | BL | BL | BL | 6.6 | 6.3 | 20.8 | 6.3 |
| MeI | BL | 0.0 | BL | 11.1 | 8.1 | 11.1 | BL | BL | 1.7 | BL |
| MeOH | 0.10 | 0.0 | 0.075 | 0.09 | 0.0 | 0.1 | 0.1 | 0.0 | 3.8 | 0.0 |
| MA | 14.1 | 0.0 | 14.1 | 0.5 | 2.7 | 0.5 | 3.8 | 3.8 | 1.5 | 3.8 |
| $H_2O$ | 0.73 | 100.0 | 0.61 | 0.1 | 0.0 | 0.1 | 1.5 | 0.2 | BL | 0.2 |
| AC | 2.01 | 0.0 | 2.0 | 0.0 | 0.0 | 0.0 | 0.0 | 0.0 | 0.0 | 0.0 |
| Total | 100.0 | 100.0 | 100.0 | 100.0 | 100.0 | 100.0 | 100.0 | 100.0 | 100.0 | 100.0 |

INDUSTRIAL APPLICABILITY

According to the present invention, PRC's (e.g., acetaldehyde) can efficiently be separated and removed, and a process significantly useful for stably producing high-quality acetic acid can be provided.

REFERENCE SIGNS LIST

1 . . . Reactor to
2 . . . Flasher (Evaporator)
3 . . . Splitter column (first distillation column)
4 . . . Decanter
5 . . . Second distillation column (separation column for PRC's such as acetaldehyde)
6a . . . Separation unit
6b . . . Hold Tank and decanter
6c . . . Decanter
7 . . . Third distillation column
8 . . . Fourth distillation column (extractive distillation column)

The invention claimed is:

1. A process for separating or removing permanganate reducing compounds (PRC's) from a first mixture containing at least one PRC, methyl iodide, and water, the process comprising the steps of:
  feeding the first mixture to a feed port of a distillation column, and
  distilling and separating the first mixture into an upper stream and a lower stream, the upper stream being at least one stream selected from the group consisting of an overhead stream and a side-cut stream,
  wherein the distillation of the first mixture allows at least a portion of water in the first mixture to rise to an upper position than the feed port to form a second mixture containing the portion of water, and
  the process further comprises the steps of: withdrawing the second mixture as the upper stream,
  withdrawing the lower stream from a lower position than the feed port, the lower stream having a water content, the water content of the lower stream being lower than that of the first mixture, and
  wherein the first mixture is separated into the upper stream and the lower stream without supply of additional water to the distillation column,
  the withdrawn upper stream is biphasically separated into an aqueous phase containing at least acetaldehyde and an organic phase containing at least methyl iodide, and
  the distillation of the first mixture comprises at least one of the following (A) and (B):
  (A) the lower stream has a ratio of water relative to methyl iodide lower than the first mixture, and
  (B) not less than 1% by weight of water in the first mixture is transferred or distributed to the upper stream, and not more than 99% by weight of water in the first mixture is transferred or distributed to the lower stream.

2. A process according to claim 1, wherein the distillation of the first mixture allows at least a portion of water in the first mixture to rise to an upper position than the feed port to form the second mixture containing the portion of water, wherein the second mixture is azeotropic, and
  the process comprises the steps of:
  withdrawing the second mixture as the upper stream, and
  withdrawing the lower stream from a lower position than the feed port, the water content of the lower stream being lower than that of the first mixture.

3. A process according to claim 1, wherein not less than 5% by weight of water in the first mixture is transferred or distributed to the upper stream, and not more than 95% by weight of water in the first mixture is transferred or distributed to the lower stream.

4. A process according to claim 1, wherein the distillation of the first mixture forms a concentration zone of the PRC's and methyl iodide at an upper position than the feed port of the distillation column and allows at least a portion of water in the first mixture to rise to the concentration zone; and a stream or fluid in the concentration zone is withdrawn as the upper stream.

5. A process according to claim 4, wherein a mixture falling from the concentration zone is withdrawn as the side-cut stream.

6. A process according to claim 1, wherein the first mixture contains 10 ppm to 30% by weight acetaldehyde, 0.1 to 90% by weight methyl iodide, and 0.1 to 90% by weight water, provided that the total amount of the first mixture, including an impurity or impurities, is 100% by weight.

7. A process according to claim 1, wherein the first mixture comprises at least a portion of an organic phase, at least a portion of an aqueous phase, or a mixture containing the organic phase and the aqueous phase, and the first mixture has a biphasically separable composition.

8. A process according to claim 1, wherein the first mixture comprises acetaldehyde, methyl iodide, and water and further comprises at least one of (a) or (b):
   (a) methyl acetate,
   (b) at least one member selected from the group consisting of acetic acid, methanol, dimethyl ether, and an acetaldehyde derivative.

9. A process according to claim 1, wherein the withdrawn upper stream is biphasically separated into an aqueous phase containing at least acetaldehyde and an organic phase containing at least methyl iodide, and the process further comprises a step of recycling the organic phase to the distillation step by the following method (a), (b), or (c):
   (a) separating the aqueous phase, and recycling the organic phase to the distillation column;
   (b) recycling a portion of the aqueous phase and the organic phase to the distillation column;
   (c) subjecting at least a portion of the aqueous phase to at least one selected from the group consisting of distillation in a succeeding distillation step and water extractive distillation in a succeeding distillation step, and directly or indirectly recycling the organic phase to the distillation column.

10. A process according to claim 1, wherein the withdrawn upper stream is biphasically separated into an aqueous phase and an organic phase, and the process further comprises the steps of:
   directly or indirectly recycling the organic phase to the distillation step,
   distilling at least a portion of the aqueous phase in a succeeding distillation step, and
   directly or indirectly feeding a miscible solvent to the distillation column, wherein the miscible solvent is miscible with the organic phase and is at least one member selected from the group consisting of water, acetic acid, methyl iodide, and methanol.

11. A process according to claim 1, the process further comprising:
   a reaction step of continuously carbonylating methanol in the presence of a catalyst system comprising a metal catalyst, a metal halide, and methyl iodide;
   a flash evaporation step of continuously separating the reaction mixture into a volatile phase and a less-volatile phase, the volatile phase containing product acetic acid and methyl iodide, and the less-volatile phase containing the metal catalyst and the metal halide;
   a distillation step of continuously separating the volatile phase into an overhead and a stream containing acetic acid, the overhead containing methyl iodide and by-product acetaldehyde; and
   a step of condensing a gaseous phase to form two phases, the gaseous phase being produced from at least one step selected from the group consisting of these steps and containing at least acetaldehyde and methyl iodide.

* * * * *